US009119813B2

(12) United States Patent
Radosevic et al.

(10) Patent No.: US 9,119,813 B2
(45) Date of Patent: *Sep. 1, 2015

(54) VACCINE AGAINST RSV

(71) Applicant: Crucell Holland B.V., Leiden (NL)

(72) Inventors: Katarina Radosevic, Leiden (NL);
Jerome H. H. V. Custers, Alphen aan den Rijn (NL); Jort Vellinga, Leiden (NL); Myra N. Widjojoatmodjo, Leiden (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/849,393

(22) Filed: Mar. 22, 2013

(65) Prior Publication Data

US 2014/0186391 A1  Jul. 3, 2014

Related U.S. Application Data

(60) Provisional application No. 61/614,429, filed on Mar. 22, 2012.

(51) Int. Cl.
| A61K 39/12 | (2006.01) |
| A61K 39/155 | (2006.01) |
| C12N 15/861 | (2006.01) |
| C12N 7/00 | (2006.01) |
| A61K 39/00 | (2006.01) |

(52) U.S. Cl.
CPC .............. *A61K 39/155* (2013.01); *A61K 39/12* (2013.01); *C12N 7/00* (2013.01); *A61K 2039/5256* (2013.01); *C12N 2710/10343* (2013.01); *C12N 2760/18534* (2013.01)

(58) Field of Classification Search
None
See application file for complete search history.

(56) References Cited

U.S. PATENT DOCUMENTS

| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,225,289 B1 | 5/2001 | Kovesdi et al. |
| 6,261,823 B1 | 7/2001 | Tang et al. |
| 6,485,958 B2 | 11/2002 | Blanche et al. |
| 7,270,811 B2 | 9/2007 | Bout et al. |
| 7,326,555 B2 | 2/2008 | Konz, Jr. et al. |
| 7,510,868 B2 | 3/2009 | Harden et al. |
| 2010/0111989 A1 | 5/2010 | Grundwald et al. |
| 2011/0014220 A1 | 1/2011 | Chow et al. |

FOREIGN PATENT DOCUMENTS

| EP | 2102345 | 3/2011 |
| WO | 9003184 | 4/1990 |
| WO | 9014837 | 12/1990 |
| WO | 9609378 | 3/1996 |
| WO | 9611711 | 4/1996 |
| WO | 9802522 | 1/1998 |
| WO | 9822588 | 5/1998 |
| WO | 9839411 | 9/1998 |
| WO | 9912568 | 3/1999 |
| WO | 9941416 | 8/1999 |
| WO | 0029024 | 5/2000 |
| WO | 0032754 | 6/2000 |
| WO | 0070071 | 11/2000 |
| WO | 0166137 | 9/2001 |
| WO | 0240665 | 5/2002 |
| WO | 03049763 | 6/2003 |
| WO | 03061708 | 7/2003 |
| WO | 03078592 | 9/2003 |
| WO | 03104467 | 12/2003 |
| WO | 04001032 | 12/2003 |
| WO | 2004004762 | 1/2004 |
| WO | 2004020971 | 3/2004 |
| WO | 2005002620 | 1/2005 |
| WO | 2005080556 | 9/2005 |
| WO | 2006086284 A2 | 8/2006 |
| WO | 2006108707 | 10/2006 |
| WO | 2007104792 | 9/2007 |
| WO | 2007110409 | 10/2007 |

(Continued)

OTHER PUBLICATIONS

GenBank: ACO83301.1. Fusion protein [Respiratory syncytial virus]. http://www.ncbi.nlm.nih.gov/protein/226838114?report=genbank&log$=protalign&blast_rank=1&RID=SA1RJKGR01R. Dated Apr. 20, 2009.*
Stillman et al. Adenoviral DNA Replication: DNA Sequences and Enzymes. Cold Spring Harb Symp Quant Biol 1983 47: 741-750.*
Groothuis et al. Safety and immunogenicity of a purified F protein respiratory syncytial virus (PFP-2) vaccine in seropositive children with bronchopulmonary dysplasia. J Infect Dis. Feb. 1998;177(2):467-9.*
Prince et al.; Enhancement of Respiratory Syncytial Virus Pulmonary Pathology in Cotton Rats by Prior Intramuscular Inoculation of Formalin-Inactivated Virus; Journal of Virology, vol. 57, No. 3; Mar. 1986; p. 721-728.

(Continued)

*Primary Examiner* — Nicole Kinsey White
*Assistant Examiner* — Nick Zou
(74) *Attorney, Agent, or Firm* — TraskBritt, P.C.

(57) ABSTRACT

Provided is a vaccine against respiratory syncytial virus (RSV), comprising a recombinant human adenovirus of serotype that comprises nucleic acid encoding a RSV F protein or immunologically active part thereof.

3 Claims, 29 Drawing Sheets

(56) References Cited

FOREIGN PATENT DOCUMENTS

| WO | 2009117134 | 9/2009 |
|---|---|---|
| WO | 2010060719 | 6/2010 |
| WO | 2011045378 | 4/2011 |
| WO | 2011045381 | 4/2011 |
| WO | 2011098592 | 8/2011 |
| WO | 2012021730 | 2/2012 |

OTHER PUBLICATIONS

Search Report for International application PCT/EP2014/055935, mailed May 28, 2013, 4 pages.

Search Report for International application PCT/EP2014/055943, mailed May 28, 2013, 4 pages.

Written Opinion for International application PCT/EP2014/055935, mailed May 28, 2013, 5 pages.

Written Opinion for International application PCT/EP2014/055943, mailed May 28, 2013, 5 pages.

Abbink et al.; Comparative Seroprevalence and Immunogenicity of Six Rare SErotype Recombinant Adenovirus Vaccine Vectors from Subgroups B and D; Journal of Virology; vol. 81, No. 9; May 2007; p. 4654-4663.

Abrahamsen et al.; Construction of an adenovirus type 7a E1A-vector; Journal of Virology; vol. 71, No. 11; Nov. 1997; p. 8946-8951.

Altaras et al.; Production and Formulation of Adenovirus Vectors; Adv Biochem Engin/Biotechnol (2005) 99: 193-260.

Brough et al.; A Gene Transfer Vector-Cell Line System for Complete Functional Complementation of Adenovirus Early Regions E1 and E4; Journal of Virology; vol. 70, No. 9; Sep. 1996, p. 6497-6501.

Collins et al.; Evaluation of the Protective Efficacy of Recombinant Vaccinia Viruses and Adenoviruses That Express Respiratory Syncytial Virus Glycoproteins; Vaccines 90; 1990 p. 79-84.

Collins et al.; Vaccines against Human REspiratory Syncytial Virus; Respiratory Syncytial Virus; 2007; p. 233-277.

Colloca et al.; Vaccine Vectors Derived from a Large Collection of Simian Adenoviruses Induce Potent Cellular Immunity Across Multiple Species; Science Translation Medicine, vol. 4 Issue 115; Jan. 4, 2012; 10 pages.

Connors et al.; Cotton rats previously immunized with a chimeric RSV GF glycoprotein develop enhanced pulmonary pathology when infected with RSV, a phenomenon not encountered following immunization with vaccinia—RSV recombinants or RSV; Vaccine, vol. 10, Issue 7, 1992; p. 475-484.

European Search Report; EP 12 16 0682; dated Jul. 24, 2012.

Fallaux et al.; New Helper Cells and Matched Early Region 1-Deleted Adenovirus Vectors Prevent Generation of Replication-Competent Adenoviruses; Human Gene Therapy 9:1909-1917 (Sep. 1, 1998).

Fu et al.; Intranasal immunization with a replication-deficient adenoviral vector expressing the fusion glycoprotein of respiratory syncytial virus elects protective immunity in BALB/c mice; Biochemical and Biophysical Research Communications 381 (2009) p. 528-532.

Gao et al.; A Cell Line for High-Yield Production of E1-Deleted Adenovirus Vectors without the Emergence of Replication-Competent Virus; Human Gene Therapy 11:213-219; Jan. 1, 2000.

Geisbert et al.; Recombinant Adenovirus Serotype 26 (Ad26) and Ad35 Vaccine Vectors Bypass Immunity to Ad5 and Protect Nonhuman Primates against Ebolavirus Challenge; Journal of Virology; vol. 85, No. 9; May 2011; p. 4222-4233.

Goerke et al.; Development of a Novel Adenovirus Purification Process Utilizing Selective Precipitation of Cellular DNA; Biologics Development & Engineering, BioProcess R&D Published online May 11, 2005 in Wiley InterScience; 10 pages.

Havenga et al.; Novel replication-incompetent adenoviral B-group vectors: high vector stability and yield in PER.C6 cells; Journal of General Virology (2006), 87, 2135-2143.

Hoganson et al.; Development of a Stable Adenoviral Vector Formulation; Bioprocessing Journal; Mar. 2002; p. 43-48.

Horowitz, Marshall S.; Adenoviruses; Fields Virology, Third Edition; Chapter 68; 1996; p. 2149-2171.

Hsu et al.; Immunogenicity of Recombinant Adenovirus-Respiratory Syncytial Virus Vaccines with Adenovirus Types 4, 5, and 7 Vectors in Dogs and Chimpanzee; JID; Oct. 1992, p. 769-775.

Johnson et al.; A Direct Comparison of the Activities of Two Humanized Respiratory Syncytial Virus Monoclonal Antibodies: MEDI-493 and RSHZ19; JID; Jul. 1999; p. 35-40.

Kim et al.; Single muxosal immunization of recombinant adenovirus-based vaccine expressing F1 protein fragment induces protective mucosal immunity against respiratory syncytial virus infection; Vaccine 28 (2010) 3801-3808.

Kohlmann et al.; Protective Efficacy and Immunogenicity of an Adenoviral Vector Vaccine Encoding the Codon-Optimized F Protein of Respiratory Syncytial Virus; Journal of Virology, vol. 83, No. 23; Dec. 2009, p. 12601-12610.

Konz et al.; Serotype Specificity of Adenovirus Purification Using Anion-Exchange Chromatography; Human Gene Therapy 16:1346-1356; Nov. 2005.

Konz et al.; Scalable Purification of Adenovirus Vectors; Methods in Molecular Biology, vol. 434, 2002; p. 13-23.

Krause et al.; Absence of vaccine-enhanced RSV disease and changes in pulmonary dendritic cells with adenovirus-based RSV vaccine; Virology Journal 2011, 8:375; 12 pages.

Nan et al.; Development of an Ad7 cosmid system and generation of an Ad7 E1 E3HIV MN env/rev recombinant virus; Gene Therapy (2003) 10, 326-336.

Niewiesk et al.; Diversifying animal models: the use of hispid cotton rats (Sigmodon hispidus) in infectious diseases; Laboratory Animals (2002) 36, 357-372.

Pemberton et al.; Cytotoxic T Cell Specificity for Respiratory Syncytial Virus Proteins: Fusion Protein Is an Important Target Antigen; J. Gen. Virol. (1987) 68, 2177-2182.

Prince et al.; The Pathogenesis of Respiratory Syncytial Virus Infection in Cotton Rats; American Journal of Pathology; 1978; p. 771-784; 6 pages of figures.

Prince et al.; Pulmonary Lesions in Primary Respiratory Syncytial Virus Infection, Reinfection, and Vaccine-Enhanced Disease in the Cotton Rat (Sigmodon hispidus); Laboratory Investigation; Nov. 1999; vol. 79, No. 11; p. 1385-1392.

Radosevic et al.; The Th1 Immune Response to *Plasmodium falciparum* Circumsporozoite Protein Is Boosted by Adenovirus Vectors 35 and 26 with a Homologous Insert; Clinical and Vaccine Immunology, vol. 17, No. 11; Nov. 2010, p. 1687-1694.

Shao et al.; Immunogenic properties of RSV-B1 fusion (F) protein gene-encoding recombinant adenoviruses; Vaccine 27 (2009) 5460-5471.

Shenk, Thomas; Adenoviridae: The Viruses and Their Replication; Fields Virology, Third Edition; Chapter 67; 1996; p. 2111-2148.

Singh et al.; Immunogenicity and efficacy of recombinant RSV-F vaccine in a mouse model; Vaccine 25 (2007) 6211-6223.

Singh et al.; Respiratory Syncytial Virus Recombinant F Protein (Residues 255-278) Induces a Helper T Cell Type 1 Immune Response in Mice; Viral Immunology; vol. 20, No. 2; 2007; p. 261-275.

Ogun et al.; The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria; Infection and Immunity, vol. 76, No. 8; Aug. 2008, p. 3817-3823.

Vogels et al.; Replication-Deficient Human Adenovirus Type 35 Vectors for Gene Transfer and Vaccination: Efficient Human Cell Infection and Bypass of Preexisting Adenovirus Immunity; Journal of Virology, vol. 77, No. 15; Aug. 2003, p. 8263-8271.

Yu et al.; Single Intranasal Immunization with Recombinant Adenovirus-Based Vaccine Induces Protective Immunity against Respiratory Syncytial Virus Infection; Journal of Virology, vol. 82, No. 5; Mar. 2008, p. 2350-2357.

Kruse & Patterson—Tissue Culture (Academic Press 1973).

Sambrook et al—Molecular Cloning, a Laboratory Manual (Spring Harbor Press 1989).

\* cited by examiner

A) Ad26-RSV.F

B) Ad35-RSV.F

A) Ad26-RSV.F

B) Ad35-RSV.F

VACCINE AGAINST RSV

CROSS-REFERENCE TO RELATED APPLICATION

This application claims the benefit under 35 U.S.C. §119 (e) of U.S. Provisional Patent Application Ser. No. 61/614,429, filed Mar. 22, 2012, the disclosure of the entirety of which is hereby incorporated herein in its entirety by this reference.

TECHNICAL FIELD

The disclosure relates to the field of biotechnology and medicine, particularly to vaccines against respiratory syncytial virus (RSV).

BACKGROUND

After discovery of the RSV in the 1950s, the virus soon became a recognized pathogen associated with lower and upper respiratory tract infections in humans. Worldwide, it is estimated that 64 million RSV infections occur each year resulting in 160.000 deaths (WHO Acute Respiratory Infections Update September 2009). The most severe disease occurs particularly in premature infants, the elderly and immunocompromised individuals. In children younger than 2 years, RSV is the most common respiratory tract pathogen, accounting for approximately 50% of the hospitalizations due to respiratory infections, and the peak of hospitalization occurs at 2-4 months of age. It has been reported that almost all children have been infected by RSV by the age of two. Repeated infection during lifetime is attributed to ineffective natural immunity. The level of RSV disease burden, mortality and morbidity in the elderly are second to those caused by nonpandemic influenza A infections.

RSV is a paramyxovirus, belonging to the subfamily of pneumovirinae. Its genome encodes for various proteins, including the membrane proteins known as RSV Glycoprotein (G) and RSV fusion (F) protein which are the major antigenic targets for neutralizing antibodies. Proteolytic cleavage of the fusion protein precursor (F0) yields two polypeptides F1 and F2 linked via disulfide bridge. Antibodies against the fusion-mediating part of the F1 protein can prevent virus uptake in the cell and thus have a neutralizing effect. Besides being a target for neutralizing antibodies, RSV F contains cytotoxic T cell epitopes (Pemberton et al., 1987, J. Gen. Virol. 68: 2177-2182).

Treatment options for RSV infection include a monoclonal antibody against the F protein of RSV. The high costs associated with such monoclonal antibodies and the requirement for administration in a hospital setting, preclude their use for prophylaxis in the at-risk population at large scale. Thus, there is a need for an RSV vaccine, which preferably can be used for the pediatric population as well as for the elderly.

Despite 50 years of research, there is still no licensed vaccine against RSV. One major obstacle to the vaccine development is the legacy of vaccine-enhanced disease in a clinical trial in the 1960s with a formalin-inactivated (FI) RSV vaccine. FI-RSV vaccinated children were not protected against natural infection and infected children experienced more severe illness than non-vaccinated children, including two deaths. This phenomenon is referred to as "enhanced disease."

Since the trial with the FI-RSV vaccine, various approaches to generate an RSV vaccine have been pursued. Attempts include classical live attenuated cold passaged or temperature sensitive mutant strains of RSV, (chimeric) protein subunit vaccines, peptide vaccines and RSV proteins expressed from recombinant viral vectors. Although some of these vaccines showed promising pre-clinical data, no vaccine has been licensed for human use due to safety concerns or lack of efficacy.

Adenovirus vectors are used for the preparation of vaccines for a variety of diseases, including disease associated with RSV infections. The following paragraphs provide examples of adenovirus-based RSV candidate vaccines that have been described.

In one approach, RSV.F has been inserted into the non-essential E3 region of replication competent adenovirus types 4, 5, and 7. Immunization in cotton rats, intranasal (i.n.) application of $10^7$ pfu, was moderately immunogenic, and protective against lower respiratory tracts against RSV challenge, but not protective against upper respiratory tract RSV challenge (Connors et al., 1992, Vaccine 10: 475-484; Collins, P. L., Prince, G. A., Camargo, E., Purcell, R. H., Chanock, R. M. and Murphy, B. R. Evaluation of the protective efficacy of recombinant vaccinia viruses and adenoviruses that express respiratory syncytial virus glycoproteins. In: Vaccines 90: Modern Approaches to New Vaccines including prevention of AIDS (Eds. Brown, F., Chanock, R. M., Ginsberg, H. and Lerner, R. A.) Cold Spring Harbor Laboratory, New York, 1990, pp 79-84). Subsequent oral immunization of a chimpanzee was poorly immunogenic (Hsu et al., 1992, J Infect Dis. 66:769-775).

In other studies (Shao et al., 2009, Vaccine 27: 5460-71; U.S. 2011/0014220), two recombinant replication incompetent adenovirus 5 vectors carrying nucleic acid encoding the transmembrane truncated (rAd-F0ΔTM) or full-length (rAd-F0) version of the F protein of the RSV-B1 strain were engineered and given via the intranasal route to BALB/c mice. Animals were primed i.n. with $10^7$ pfu and boosted 28 days later with the same dose i.n. Although the anti-RSV-B1 antibodies were neutralizing and cross-reacting with RSV-Long and RSV-A2 strain, immunization with these vectors protected only partially against RSV B1 challenge replication. The (partial) protection with rAd-F0ΔTM was slightly higher than with rAd-F0.

In another study, it was observed that BALB/c mice i.n. immunization with $10^{11}$ virus particles with the replication deficient (Ad5 based) FG-Ad adenovirus expressing wild type RSV F (FG-Ad-F) reduced lung viral titers only a 1.5 log 10 compared with the control group (Fu et al., 2009, Biochem. Biophys. Res. Commun. 381: 528-532.

In yet other studies, it was observed that intranasally applied recombinant Ad5-based replication-deficient adenovector expressing codon optimized soluble F1 fragment of F protein of RSV A2 (amino acid 155-524) ($10^8$ PFU) could reduce RSV challenge replication in the lungs of BALB/c mice compared to control mice, but mice immunized by the intramuscular (i.m.) route did not exhibit any protection from the challenge (Kim et al., 2010, Vaccine 28: 3801-3808).

In other studies, adenovectors Ad5-based carrying the codon optimized full-length RSV F (AdV-F) or the soluble form of the RSF F gene (AdV-Fsol) were used to immunize BALB/c mice twice with a dose of $1 \times 10^{10}$ OPU (optical particle units: a dose of $1 \times 10^{10}$ OPU corresponds with $2 \times 10^8$ GTU (gene transduction unit)). These vectors strongly reduced viral loads in the lungs after i.n. immunization, but only partially after subcutaneous (s.c.) or i.m. application (Kohlmann et al., 2009, J Virol 83: 12601-12610; U.S. 2010/0111989).

In yet other studies, it was observed that intramuscular applied recombinant Ad5-based replication-deficient adenovector expressing the sequenced F protein cDNA of RSV A2 strain ($10^{10}$ particle units) could reduce RSV challenge replication only partially in the lungs of BALB/c mice compared to control mice (Krause et al., 2011, *Virology Journal* 8:375-386)

Apart from not being fully effective in many cases, the RSV vaccines under clinical evaluation for pediatric use and most of the vaccines under pre-clinical evaluation, are intranasal vaccines. The most important advantages of the intranasal strategy are the direct stimulation of local respiratory tract immunity and the lack of associated disease enhancement. Indeed, generally the efficacy of, for instance, the adenovirus based RSV candidate vaccines appears better for intranasal administration as compared to intramuscular administration. However, intranasal vaccination also gives rise to safety concerns in infants younger than 6 months. Most common adverse reactions of intranasal vaccines are runny nose or nasal congestion in all ages. Newborn infants are obligate nasal breathers and thus must breathe through the nose. Therefore, nasal congestion in an infant's first few months of life can interfere with nursing, and in rare cases can cause serious breathing problems.

More than 50 different human adenovirus serotypes have been identified. Of these, adenovirus serotype 5 (Ad5) has historically been studied most extensively for use as gene carrier. Recombinant adenoviral vectors of different serotypes may however give rise to different results with respect to induction of immune responses and protection. For instance, WO 2012/021730 describes that simian adenoviral vector serotype 7 and human adenoviral vector serotype 5 encoding F protein provide better protection against RSV than a human adenoviral vector of serotype 28. In addition, differential immunogenicity was observed for vectors based on human or non-human adenovirus serotypes (Abbink et al., 2007, *J Virol* 81: 4654-4663; Colloca et al., 2012, *Sci Trans' Med* 4, 115ra2). Abbink et al. conclude that all rare serotype human rAd vectors studied were less potent than rAd5 vectors in the absence of anti-Ad5 immunity. Further, it has been recently described that, while rAd5 with an Ebolavirus (EBOV) glycoprotein (gp) transgene protected 100% of non-human primates, rAd35 and rAd26 with EBOV gp transgene provided only partial protection and a heterologous prime-boost strategy was required with these vectors to obtain full protection against ebola virus challenge (Geisbert et al., 2011, *J Virol* 85: 4222-4233). Thus, it is a priori not possible to predict the efficacy of a recombinant adenoviral vaccine, based solely on data from another adenovirus serotype.

Moreover, for RSV vaccines, experiments in appropriate disease models such as cotton rat are required to determine if a vaccine candidate is efficacious enough to prevent replication of RSV in the nasal tract and lungs and at the same time is safe, i.e., does not lead to enhanced disease.

SUMMARY OF THE DISCLOSURE

It was surprisingly found by the present inventors that recombinant adenoviruses of serotype 35 (Ad35) that comprise a polynucleotide encoding RSV F protein are very effective vaccines against RSV in a well established cotton rat model, and have improved efficacy as compared to data described earlier for Ad5 encoding RSV F. It is demonstrated that even a single administration, even intramuscularly, of Ad35 encoding RSV F is sufficient to provide complete protection against challenge RSV replication.

Provided is a vaccine against respiratory syncytial virus (RSV), comprising a recombinant human adenovirus of serotype 35 that comprises nucleic acid encoding a RSV F protein or fragment thereof.

In certain embodiments, the recombinant adenovirus comprises nucleic acid encoding RSV F protein that comprises the peptide of SEQ ID NO:1 of the Sequence Listing, which incorporated by reference herein.

In certain embodiments, the nucleic acid encoding RSV F protein is codon optimized for expression in human cells. In certain such embodiments, the nucleic acid encoding RSV F protein comprises the polynucleotide of SEQ ID NO:2.

In certain embodiments, the recombinant human adenovirus has a deletion in the E1 region, a deletion in the E3 region, or a deletion in both the E1 and the E3 regions of the adenoviral genome.

In certain embodiments, the recombinant adenovirus has a genome comprising at its 5' terminal ends the sequence CTATCTAT.

Further provided is a method for vaccinating a subject against RSV, the method comprising administering to the subject a vaccine hereof.

In certain embodiments, the vaccine is administered intramuscularly.

In certain embodiments, a vaccine hereof is administered to the subject more than once.

In certain embodiments, the method for vaccination consists of a single administration of the vaccine to the subject.

In certain embodiments, the method for vaccinating a subject against RSV further comprises administering to the subject a vaccine comprising a recombinant human adenovirus of serotype 26 that comprises nucleic acid encoding a RSV F protein or fragment thereof.

In certain embodiments, the method of vaccinating a subject against RSV further comprises administering RSV F protein (preferably formulated as a pharmaceutical composition, thus, a protein vaccine) to the subject.

Also provided is a method for reducing infection and/or replication of RSV in, e.g., the nasal tract and lungs of, a subject, the method comprising administering to the subject by intramuscular injection of a composition comprising a recombinant human adenovirus of serotype 35 comprising nucleic acid encoding a RSV F protein or fragment thereof. This method will reduce adverse effects resulting from RSV infection in a subject, and thus contribute to protection of the subject against such adverse effects upon administration of the vaccine. In certain embodiments, adverse effects of RSV infection may be essentially prevented, i.e., reduced to such low levels that they are not clinically relevant. The recombinant adenovirus may be in the form of a vaccine hereof, including the embodiments described above.

Also provided is an isolated host cell comprising a recombinant human adenovirus of serotype 35 comprising nucleic acid encoding a RSV F protein or fragment thereof.

Further provided is a method for making a vaccine against respiratory syncytial virus (RSV), comprising providing a recombinant human adenovirus of serotype 35 that comprises nucleic acid encoding a RSV F protein or fragment thereof, propagating said recombinant adenovirus in a culture of host cells, isolating and purifying the recombinant adenovirus, and formulating the recombinant adenovirus in a pharmaceutically acceptable composition. The recombinant human adenovirus of this aspect may also be any of the adenoviruses described in the embodiments above.

Also provided is an isolated recombinant nucleic acid that forms the genome of a recombinant human adenovirus of serotype 35 that comprises nucleic acid encoding a RSV F protein or fragment thereof. The adenovirus may also be any of the adenoviruses as described in the embodiments above.

DETAILED DESCRIPTION

Figure 1A:
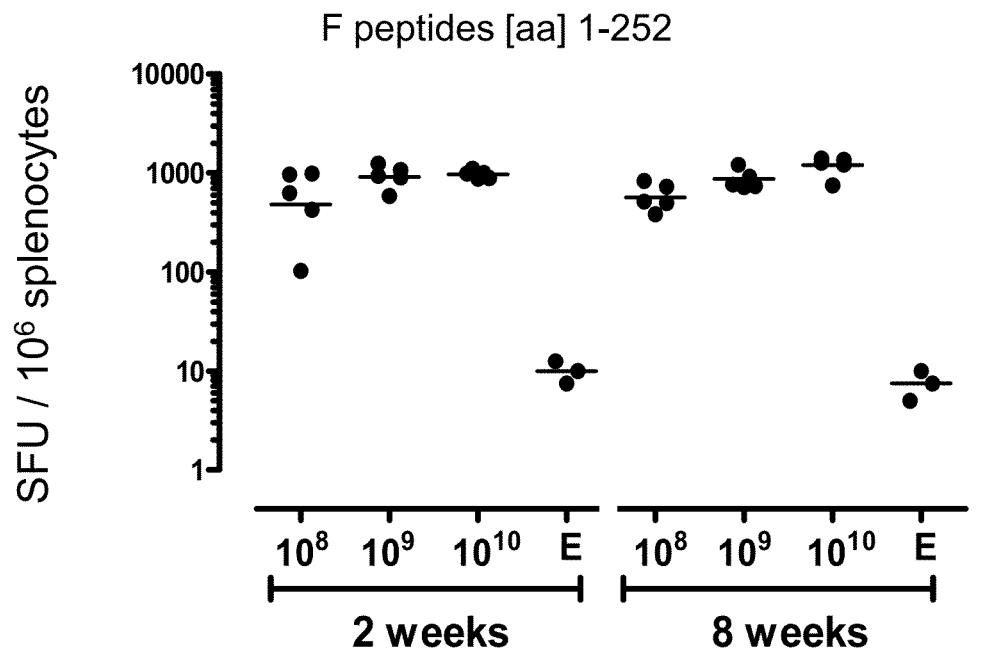
FIG. 1 shows the cellular immune response against F peptides overlapping the aa 1-252 of F and F peptides overlapping the aa 241-574 of F of mice upon immunization with different doses of rAd26 (A) and rAd35 (B) based vectors harboring the RSV F gene at 2 and 8 weeks after immunization

The term "recombinant" for an adenovirus, as used herein implicates that it has been modified by the hand of man, e.g., it has altered terminal ends actively cloned therein and/or it comprises a heterologous gene, i.e., it is not a naturally occurring wild type adenovirus.

Sequences herein are provided from 5' to 3' direction, as custom in the art.

An "adenovirus capsid protein" refers to a protein on the capsid of an adenovirus that is involved in determining the serotype and/or tropism of a particular adenovirus. Adenoviral capsid proteins typically include the fiber, penton and/or hexon proteins. An adenovirus of (or "based upon") a certain serotype hereof typically comprises fiber, penton and/or hexon proteins of that certain serotype, and preferably comprises fiber, penton and hexon protein of that certain serotype. These proteins are typically encoded by the genome of the recombinant adenovirus. A recombinant adenovirus of a certain serotype may optionally comprise and/or encode other proteins from other adenovirus serotypes. Thus, as a non-limiting example, a recombinant adenovirus that comprises hexon, penton and fiber of Ad35 is considered a recombinant adenovirus based upon Ad35.

A recombinant adenovirus is "based upon" an adenovirus as used herein, by derivation from the wild type, at least in sequence. This can be accomplished by molecular cloning, using the wild type genome or parts thereof as starting material. It is also possible to use the known sequence of a wild type adenovirus genome to generate (parts of) the genome de novo by DNA synthesis, which can be performed using routine procedures by service companies having business in the field of DNA synthesis and/or molecular cloning (e.g., Gene-Art, Invitrogen, GenScripts, Euro fins).

It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a polynucleotide or nucleic acids encoding a peptide includes all polynucleotides that are degenerate versions of each other and that encode the same peptide. Polynucleotides that encode proteins and RNA may include introns.

In certain embodiments, the nucleic acid encoding the RSV F protein or fragment thereof is codon optimized for expression in mammalian cells, such as human cells. Methods of codon-optimization are known and have been described previously (e.g., WO 96/09378). An example of a specific codon-optimized sequence of RSV F protein is described in SEQ ID NO:2 of EP 2102345 B1.

In one embodiment, the RSV F protein is from an RSV A2 strain, and has the sequence of SEQ ID NO:1. In a particularly preferred embodiment, the nucleic acid encoding the RSV F protein comprises the polynucleotide of SEQ ID NO:2. It was found by the inventors that this embodiment results in stable expression and that a vaccine according to this embodiment provides protection to RSV replication in the nasal tract and lungs even after a single dose that was administered intramuscularly.

The term "fragment" as used herein refers to a peptide that has an amino-terminal and/or carboxy-terminal and/or internal deletion, but where the remaining peptide is identical to the corresponding positions in the sequence of a RSV F protein, for example, the full-length sequence of a RSV F protein. It will be appreciated that for inducing an immune response and in general for vaccination purposes, a protein needs not to be full length nor have all its wild type functions, and fragments of the protein are equally useful. Indeed, fragments of RSV F protein like F1 or F soluble have been shown to be efficacious in inducing immune responses like full-length F (Shao et al., 2009, *Vaccine* 27: 5460-71, Kohlmann et al., 2009, *J Virol* 83: 12601-12610). Incorporation of F-protein fragments corresponding to the amino acids 255-278 or 412-524 into active immunization induce neutralizing antibodies and some protection against RSV challenge (Sing et al., 2007, *Virol. Immunol.* 20, 261-275; Sing et al., 2007, Vaccine 25, 6211-6223).

A fragment hereof is an immunologically active fragment, and typically comprises at least 15 amino acids, or at least 30 amino acids, of the RSV F protein. In certain embodiments, it comprises at least 50, 75, 100, 150, 200, 250, 300, 350, 400, 450, 500, or 550 amino acids, of the RSV F protein.

The person skilled in the art will also appreciate that changes can be made to a protein, e.g., by amino acid substitutions, deletions, additions, etc., e.g., using routine molecular biology procedures. Generally, conservative amino acid substitutions may be applied without loss of function or immunogenicity of a polypeptide. This can be checked according to procedures known to the skilled person.

The term "vaccine" refers to an agent or composition containing an active component effective to induce a therapeutic degree of immunity in a subject against a certain pathogen or disease. In this disclosure, the vaccine comprises an effective amount of a recombinant adenovirus that encodes an RSV F protein, or an antigenic fragment thereof, which results in an immune response against the F protein of RSV. This provides a method of preventing serious lower respiratory tract disease leading to hospitalization and the decrease the frequency of complications such as pneumonia and bronchiolitis due to RSV infection and replication in a subject. Thus, also provided is a method for preventing or reducing serious lower respiratory tract disease, preventing or reducing (e.g., shortening) hospitalization, and/or reducing the frequency and/or severity of pneumonia or bronchiolitis caused by RSV in a subject, comprising administering to the subject by intramuscular injection of a composition comprising a recombinant human adenovirus of serotype 35 comprising nucleic acid encoding a RSV F protein or fragment thereof. The term "vaccine" hereof implies that it is a pharmaceutical composition, and, thus, typically includes a pharmaceutically acceptable diluent, carrier or excipient. It may or may not comprise further active ingredients. In certain embodiments it may be a combination vaccine that further comprises other components that induce an immune response, e.g., against other proteins of RSV and/or against other infectious agents.

The vectors hereof are recombinant adenoviruses, also referred to as recombinant adenoviral vectors. The preparation of recombinant adenoviral vectors is well known in the art.

In certain embodiments, an adenoviral vector hereof is deficient in at least one essential gene function of the E1 region, e.g., the E1a region and/or the E1b region, of the adenoviral genome that is required for viral replication. In certain embodiments, an adenoviral vector hereof is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication," M. S. Horwitz, "Adenoviruses," Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989), Watson et al., *Recombinant DNA*, 2d ed., Scientific American Books (1992), and Ausubel et al., *Current Protocols in Molecular Biology*, Wiley Interscience Publishers, NY (1995), and other references mentioned herein. All patents, patent applications, and publications cited herein are incorporated herein by this reference.

As used herein, an adenovirus is a human adenovirus of the serotype 35. The vaccines hereof based on this serotype as well as those based on Ad26 surprisingly appear more potent than the ones described in the prior art that were based on Ad5, since those failed to provide complete protection against RSV challenge replication after a single intramuscular administration (Kim et al., 2010, Vaccine 28: 3801-3808; Kohlmann et al., 2009, *J Virol* 83: 12601-12610; Krause et al., 2011, *Virology Journal* 8:375). The serotype hereof further generally has a low seroprevalence and/or low pre-existing neutralizing antibody titers in the human population. Recombinant adenoviral vectors of this serotype and of Ad26 with different transgenes are evaluated in clinical trials, and thus far show to have an excellent safety profile. Preparation of rAd26 vectors is described, for example, in WO 2007/104792 and in Abbink et al., (2007) *Virol* 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., (2003) *J Virol* 77(15): 8263-71. Exemplary genome sequences of Ad35 are found in GenBank Accession AC_000019 and in FIG. 6 of WO 00/70071.

A recombinant adenovirus hereof may be replication-competent or replication-deficient.

In certain embodiments, the adenovirus is replication deficient, e.g., because it contains a deletion in the E1 region of the genome. As known to the skilled person, in case of deletions of essential regions from the adenovirus genome, the functions encoded by these regions have to be provided in trans, preferably by the producer cell, i.e., when parts or whole of E1, E2 and/or E4 regions are deleted from the adenovirus, these have to be present in the producer cell, for instance, integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as "packaging cell" or "complementing cell" or "host cell") that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g., 911 or PER.C6® cells (see U.S. Pat. No. 5,994,128), E1-transformed amniocytes (See EP Patent 1230354), E1-transformed A549 cells (see e.g., WO 98/39411, U.S. Pat. No. 5,891,690), GH329:HeLa (Gao et al., 2000, *Human Gene Therapy* 11: 213-219), 293, and the like. In certain embodiments, the producer cells are, for instance, HEK293 cells, or PER.C6® cells, or 911 cells, or IT293SF cells, and the like.

For non-subgroup C E1-deficient adenoviruses such as Ad35 (subgroup B) or Ad26 (subgroup D), it is preferred to exchange the E4-orf6 coding sequence of these non-subgroup C adenoviruses with the E4-orf6 of an adenovirus of subgroup C such as Ad5. This allows propagation of such adenoviruses in well known complementing cell lines that express the E1 genes of Ad5, such as, for example, 293 cells or PER.C6® cells (see, e.g., Havenga et al., 2006, *J. Gen. Virol.* 87: 2135-2143; WO 03/104467, incorporated in its entirety by reference herein). In certain embodiments, the adenovirus in the vaccine composition is a human adenovirus of serotype 35, with a deletion in the E1 region into which the nucleic acid encoding RSV F protein antigen has been cloned, and with an E4 orf6 region of Ad5. In certain embodiments, an adenovirus in that can be used is a human adenovirus of serotype 26, with a deletion in the E1 region into which the nucleic acid encoding RSV F protein antigen has been cloned, and with an E4 orf6 region of Ad5.

In alternative embodiments, there is no need to place a heterologous E4orf6 region (e.g., of Ad5) in the adenoviral vector, but instead the E1-deficient non-subgroup C vector is propagated in a cell line that expresses both E1 and a compatible E4orf6, e.g., the 293-ORF6 cell line that expresses both E1 and E4orf6 from Ad5 (see e.g., Brough et al., 1996, *J Virol* 70: 6497-501 describing the generation of the 293-ORF6 cells; Abrahamsen et al., 1997, *J Virol* 71: 8946-51 and Nan et al., 2003, *Gene Therapy* 10: 326-36 each describing generation of E1 deleted non-subgroup C adenoviral vectors using such a cell line).

Alternatively, a complementing cell that expresses E1 from the serotype that is to be propagated can be used (see e.g., WO 00/70071, WO 02/40665).

For subgroup B adenoviruses, such as Ad35, having a deletion in the E1 region, it is preferred to retain the 3' end of the E1B 55K open reading frame in the adenovirus, for instance, the 166 bp directly upstream of the pIX open reading frame or a fragment comprising this such as a 243 bp fragment directly upstream of the pIX start codon (marked at the 5' end by a Bsu36I restriction site in the Ad35 genome), since this increases the stability of the adenovirus because the promoter of the pIX gene is partly residing in this area (see, e.g., Havenga et al., 2006, *J Gen. Virol.* 87: 2135-2143; WO 2004/001032, incorporated by reference herein).

"Heterologous nucleic acid" (also referred to herein as "transgene") in adenoviruses hereof is nucleic acid that is not naturally present in the adenovirus. It is introduced into the adenovirus, for instance, by standard molecular biology techniques. In this disclosure, the heterologous nucleic acid encodes RSV F protein or fragment thereof. It can, for instance, be cloned into a deleted E1 or E3 region of an adenoviral vector. A transgene is generally operably linked to expression control sequences. This can, for instance, be done by placing the nucleic acid encoding the transgene(s) under the control of a promoter. Further regulatory sequences may be added. Many promoters can be used for expression of a transgene(s), and are known to the skilled person. A non-limiting example of a suitable promoter for obtaining expression in eukaryotic cells is a CMV-promoter (U.S. Pat. No. 5,385,839), e.g., the CMV immediate early promoter, for instance, comprising nt. −735 to +95 from the CMV immediate early gene enhancer/promoter. A polyadenylation signal, for example, the bovine growth hormone polyA signal (U.S. Pat. No. 5,122,458), may be present behind the transgene(s).

In certain embodiments, the recombinant Ad26 or Ad35 vectors hereof comprise as the 5' terminal nucleotides the polynucleotide: CTATCTAT. These embodiments are advantageous because such vectors display improved replication in production processes, resulting in batches of adenovirus with improved homogeneity, as compared to vectors having the original 5' terminal sequences (generally CATCATCA) (see also Patent Application Nos. PCT/EP2013/054846 and U.S. Ser. No. 13/794,318, entitled "Batches of recombinant adenovirus with altered terminal ends" filed on Mar. 12, 2012 in the name of Crucell Holland B. V.), incorporated in its entirety by reference herein. Thus, also provided are batches of recombinant adenovirus encoding RSV F protein or a part thereof, wherein the adenovirus is a human adenovirus serotype 35, and wherein essentially all (e.g., at least 90%) of the adenoviruses in the batch comprise a genome with terminal polynucleotide CTATCTAT.

For use herein, the F protein of RSV may be derived from any strains of naturally-occurring or recombinant RSV, preferably from human RSV strains, such as A2, Long, or B strains. In further embodiments, the sequence may be a consensus sequence based upon a plurality of RSV F protein peptides. In one example hereof, the RSV strain is RSV-A2 strain.

For use herein, the F protein of RSV may be the full length of F protein of RSV, or fragment thereof. In one embodiment hereof, the polynucleotide encoding F protein of RSV encodes the full length of F protein of RSV (F0), such as the amino acid of SEQ ID NO:1. In one example hereof, the polynucleotide encoding F protein of RSV has the polynucleotide of SEQ ID NO:2. Alternatively, the sequence encoding F protein of RSV may be any sequence that is at least about 80%, preferably more than about 90%, more preferably at least about 95%, identical to the polynucleotide of SEQ ID NO:2. In other embodiments, codon-optimized sequences such as, for instance, provided in SEQ ID NO:2, 4, 5 or 6 of WO 2012/021730 can be used.

In another embodiment hereof, the polynucleotide may alternatively encode a fragment of F protein of RSV. The fragment may result from either or both of amino-terminal and carboxy-terminal deletions. The extent of deletion may be determined by a person skilled in the art to, for example, achieve better yield of the recombinant adenovirus. The fragment will be chosen to comprise an immunologically active fragment of the F protein, i.e., a part that will give rise to an immune response in a subject. This can be easily determined using in silico, in vitro and/or in vivo methods, all routine to the skilled person. In one embodiment hereof, the fragment is a transmembrane coding region-truncated F protein of RSV (F0ΔTM, see e.g., U.S. 20110014220). The fragments of F protein may also be F1 domain or F2 domain of F protein. The fragments of F may also be fragments containing neutralization epitopes and T cell epitopes (Sing et al., 2007, *Virol. Immunol.* 20, 261-275; Sing et al., 2007, *Vaccine* 25, 6211-6223).

The term "about" for numerical values as used in the present disclosure means the value±10%.

In certain embodiments, provided are methods for making a vaccine against respiratory syncytial virus (RSV), comprising providing a recombinant human adenovirus of serotype 35 that comprises nucleic acid encoding a RSV F protein or fragment thereof, propagating said recombinant adenovirus in a culture of host cells, isolating and purifying the recombinant adenovirus, and bringing the recombinant adenovirus in a pharmaceutically acceptable composition.

Recombinant adenovirus can be prepared and propagated in host cells, according to well known methods, which entail cell culture of the host cells that are infected with the adenovirus. The cell culture can be any type of cell culture, including adherent cell culture, e.g., cells attached to the surface of a culture vessel or to microcarriers, as well as suspension culture.

Most large-scale suspension cultures are operated as batch or fed-batch processes because they are the most straightforward to operate and scale up. Nowadays, continuous processes based on perfusion principles are becoming more common and are also suitable (see e.g., WO 2010/060719, and WO 2011/098592, both incorporated by reference herein, which describe suitable methods for obtaining and purifying large amounts of recombinant adenoviruses).

Producer cells are cultured to increase cell and virus numbers and/or virus titers. Culturing a cell is done to enable it to metabolize, and/or grow and/or divide and/or produce virus of interest hereof. This can be accomplished by methods as such well known to persons skilled in the art, and includes but is not limited to providing nutrients for the cell, for instance, in the appropriate culture media. Suitable culture media are well known to the skilled person and can generally be obtained from commercial sources in large quantities, or custom-made according to standard protocols. Culturing can be done, for instance, in dishes, roller bottles or in bioreactors, using batch, fed-batch, continuous systems and the like. Suitable conditions for culturing cells are known (see e.g., Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Typically, the adenovirus will be exposed to the appropriate producer cell in a culture, permitting uptake of the virus. Usually, the optimal agitation is between about 50 and 300 rpm, typically about 100-200, e.g., about 150, typical DO is 20-60%, e.g., 40%, the optimal pH is between 6.7 and 7.7, the optimal temperature between 30 and 39° C., e.g., 34-37° C., and the optimal MOI between 5 and 1000, e.g., about 50-300. Typically, adenovirus infects producer cells spontaneously, and bringing the producer cells into contact with rAd particles is sufficient for infection of the cells. Generally, an adenovirus seed stock is added to the culture to initiate infection, and subsequently the adenovirus propagates in the producer cells. This is all routine for the person skilled in the art.

After infection of an adenovirus, the virus replicates inside the cell and is thereby amplified, a process referred to herein as propagation of adenovirus. Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g., U.S. Pat. No. 6,485,958, describing the harvesting of adenovirus without lysis of the host cells by an external factor). It is preferred to employ external factors to actively lyse the cells for harvesting the adenovirus.

Methods that can be used for active cell lysis are known to the person skilled in the art, and have, for instance, been discussed in WO 98/22588, p. 28-35. Useful methods in this respect are, for example, freeze-thaw, solid shear, hypertonic and/or hypotonic lysis, liquid shear, sonication, high pressure extrusion, detergent lysis, combinations of the above, and the like. In one embodiment hereof, the cells are lysed using at least one detergent. Use of a detergent for lysis has the advantage that it is an easy method, and that it is easily scalable.

Detergents that can be used, and the way they are employed, are generally known to the person skilled in the art. Several examples are, for instance, discussed in WO 98/22588, p. 29-33. Detergents can include anionic, cationic, zwitterionic, and nonionic detergents. The concentration of the detergent may be varied, for instance, within the range of about 0.1%-5% (w/w). In one embodiment, the detergent used is Triton X-100.

Nuclease may be employed to remove contaminating, i.e., mostly from the producer cell, nucleic acids. Exemplary nucleases suitable for use in this disclosure include BENZONASE®, PULMOZYME®, or any other DNase and/or RNase commonly used within the art. In preferred embodiments, the nuclease is BENZONASE®, which rapidly hydrolyzes nucleic acids by hydrolyzing internal phosphodiester bonds between specific nucleotides, thereby reducing the viscosity of the cell lysate. BENZONASE® can be commercially obtained from Merck KGaA (code W214950). The concentration in which the nuclease is employed is preferably within the range of 1-100 units/ml. Alternatively, or in addition to nuclease treatment, it is also possible to selectively precipitate host cell DNA away from adenovirus preparations during adenovirus purification, using selective precipitating agents such as domiphen bromide (see e.g., U.S. Pat. No. 7,326,555; Goerke et al., 2005, Biotechnology and bioengineering, Vol. 91: 12-21; WO 2011/045378; WO 2011/045381).

Methods for harvesting adenovirus from cultures of producer cells have been extensively described in WO 2005/080556.

In certain embodiments, the harvested adenovirus is further purified. Purification of the adenovirus can be performed in several steps comprising clarification, ultrafiltration, diafiltration or separation with chromatography as described in, for instance, WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to find the optimal conditions for each purification step. Also WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Preferably, purification employs at least one chromatography step, as, for instance, discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process. It is, for instance, possible to purify adenoviruses by anion exchange chromatography steps, see, for instance, WO 2005/080556 and Konz et al., 2005, *Hum Gene Ther* 16: 1346-1353. Many other adenovirus purification methods have been described and are within the reach of the skilled person. Further methods for producing and purifying adenoviruses are disclosed in, for example, (WO 00/32754; WO 04/020971; U.S. Pat. No. 5,837,520; U.S. Pat. No. 6,261,823; WO 2006/108707; Konz et al., 2008, *Methods Mol Biol* 434: 13-23; Altaras et al., 2005, *Adv Biochem Eng Biotechnol* 99: 193-260), all incorporated by reference herein.

For administering to humans, pharmaceutical compositions may be employed comprising the rAd and a pharmaceutically acceptable carrier or excipient. In the present context, the term "pharmaceutically acceptable" means that the carrier or excipient, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). The purified rAd preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g., pH 5.0 to 7.5. The rAd typically is in a solution having a suitable pharmaceutically acceptable buffer, and the solution of rAd may also contain a salt. Optionally, stabilizing agent may be present, such as albumin. In certain embodiments, detergent is added. In certain embodiments, rAd may be formulated into an injectable preparation. These formulations contain effective amounts of rAd, are either sterile liquid solutions, liquid suspensions or lyophilized versions and optionally contain stabilizers or excipients. An adenovirus vaccine can also be aerosolized for intranasal administration (see e.g., WO 2009/117134).

For instance, adenovirus may be stored in the buffer that is also used for the Adenovirus World Standard (Hoganson et al., Development of a stable adenoviral vector formulation, *Bioprocessing* March 2002, p. 43-48): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Obviously, many other buffers can be used, and several examples of suitable formulations for the storage and for pharmaceutical administration of purified (adeno)virus preparations can, for instance, be found in European Patent 0853660, U.S. Pat. No. 6,225,289 and in international patent applications WO 99/41416, WO 99/12568, WO 00/29024, WO 01/66137, WO 03/049763, WO 03/078592, WO 03/061708.

In certain embodiments, a composition comprising the adenovirus further comprises one or more adjuvants. Adjuvants are known in the art to further increase the immune response to an applied antigenic determinant, and pharmaceutical compositions comprising adenovirus and suitable adjuvants are, for instance, disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the adenovirus vectors hereof. Examples of suitable adjuvants include aluminum salts such as aluminum hydroxide and/or aluminum phosphate; oil-emulsion compositions (or oil-in-water compositions), including squalene-water emulsions, such as MF59 (see e.g., WO 90/14837); saponin formulations, such as, for example, QS21 and Immunostimulating Complexes (ISCOMS) (see e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, and the like. It is also possible to use vector-encoded adjuvant, e.g., by using heterologous nucleic acid that encodes a fusion of the oligomerization domain of C4-binding protein (C4 bp) to the antigen of interest (e.g., Solabomi et al., 2008, Infect Immun 76: 3817-23). In certain embodiments the compositions hereof comprise aluminum as an adjuvant, e.g., in the form of aluminum hydroxide, aluminum phosphate, aluminum potassium phosphate, or combinations thereof, in concentrations of 0.05-5 mg, e.g., from 0.075-1.0 mg, of aluminum content per dose.

In other embodiments, the compositions do not comprise adjuvants.

It is also possible hereof to administer further active components, in combination with the vaccines hereof. Such further active components may comprise e.g., other RSV antigens or vectors comprising nucleic acid encoding these. Such vectors may be non-adenoviral or adenoviral, of which the latter can be of any serotype. An example of other RSV antigens includes RSV G protein or immunologically active parts thereof. For instance, intranasally applied recombinant replication-deficient Ad5 based adenovector rAd/3xG, expressing the soluble core domain of G glycoprotein (amino acids 130 to 230) was protective in a murine model (Yu et al., 2008, J Virol 82: 2350-2357), and although it was not protective when applied intramuscularly, it is clear from these data that RSV G is a suitable antigen for inducing protective responses. Further active components may also comprise non-RSV antigens, e.g., from other pathogens such as viruses, bacteria, parasites, and the like. The administration of further active components may, for instance, be done by separate administration or by administering combination products of the vaccines hereof and the further active components. In certain embodiments, further non-adenoviral antigens (besides RSV.F), may be encoded in the vectors hereof. In certain embodiments, it may, thus, be desired to express more than one protein from a single adenovirus, and in such cases more coding sequences, for instance, may be linked to form a single transcript from a single expression cassette or may be present in two separate expression cassettes cloned in different parts of the adenoviral genome.

Adenovirus compositions may be administered to a subject, e.g., a human subject. The total dose of the adenovirus provided to a subject during one administration can be varied as is known to the skilled practitioner, and is generally between $1 \times 10^7$ viral particles (vp) and $1 \times 10^{12}$ vp, preferably between $1 \times 10^8$ vp and $1 \times 10^{11}$ vp, for instance, between $3 \times 10^8$ and $5 \times 10^{10}$ vp, for instance, between $10^9$ and $3 \times 10^{10}$ vp.

Administration of adenovirus compositions can be performed using standard routes of administration. Non-limiting embodiments include parenteral administration, such as by injection e.g., intradermal, intramuscular, etc, or subcutaneous, transcutaneous, or mucosal administration, e.g., intranasal, oral, and the like. Intranasal administration has generally been seen as a preferred route for vaccines against RSV. The most important advantage of the live intrasal strategy is the direct stimulation of local respiratory tract immunity and the lack of associated disease enhancement. The only vaccines under clinical evaluation for pediatric use at the present time are live intranasal vaccine (Collins and Murphy. Vaccines against human respiratory syncytial virus). In: Perspectives in Medical Virology 14: Respiratory Syncytial Virus (Ed. Cane, P.), Elsevier, Amsterdam, the Netherlands, pp. 233-277). Intranasal administration is a suitable preferred route according to this disclosure as well. However, it is particularly preferred according to this disclosure to administer the vaccine intramuscularly, since it was surprisingly found that intramuscular administration of the vaccine hereof resulted in protection against RSV replication in nose and lungs of cotton rats, unlike earlier reported intramuscular RSV vaccines based on other adenovirus serotypes. The advantage of intramuscular administration is that it is simple and well-established, and does not carry the safety concerns for intranasal application in infants younger than 6 months. In one embodiment a composition is administered by intramuscular injection, e.g., into the deltoid muscle of the arm, or vastus lateralis muscle of the thigh. The skilled person knows the various possibilities to administer a composition, e.g., a vaccine in order to induce an immune response to the antigen(s) in the vaccine.

A subject as used herein preferably is a mammal, for instance, a rodent, e.g., a mouse, a cotton rat, or a non-human-primate, or a human. Preferably, the subject is a human subject. The subject can be of any age, e.g., from about 1 month to 100 years old, e.g., from about 2 months to about 80 years old, e.g., from about 1 month to about 3 years old, from about 3 years to about 50 years old, from about 50 years to about 75 years old, etc.

It is also possible to provide one or more booster administrations of one or more adenovirus vaccines hereof. If a boosting vaccination is performed, typically, such a boosting vaccination will be administered to the same subject at a moment between one week and one year, preferably between two weeks and four months, after administering the composition to the subject for the first time (which is in such cases referred to as "priming vaccination"). In alternative boosting regimens, it is also possible to administer different vectors, e.g., one or more adenoviruses of different serotype, or other vectors such as MVA, or DNA, or protein, to the subject after the priming vaccination. It is, for instance, possible to administer to the subject a recombinant adenoviral vector hereof as a prime, and boosting with a composition comprising RSV F protein.

In certain embodiments, the administration comprises a priming and at least one booster administration. In certain embodiments thereof, the priming administration is with a rAd35 comprising nucleic acid encoding RSV F protein hereof ("rAd35-RSV.F") and the booster administration is with a rAd26 comprising nucleic acid encoding RSV F protein ("rAd26-RSV.F"). In other embodiments thereof, the priming administration is with rAd26-RSV.F and the booster administration is with rAd35-RSV.F. In other embodiments, both the priming and booster administration are with rAd35.RSV.F. In certain embodiments, the priming administration is with rAd35-RSV.F and the booster administration is with RSV F protein. In all these embodiments, it is possible to provide further booster administrations with the same or other vectors or protein. Embodiments where boosting with RSV F protein may be particularly beneficial include e.g., in elder subjects in risk groups (e.g., having COPD or asthma) of 50 years or older, or e.g., in healthy subjects of 60 years or older or 65 years or older.

In certain embodiments, the administration comprises a single administration of a recombinant adenovirus hereof, without further (booster) administrations. Such embodiments are advantageous in view of the reduced complexity and costs of a single administration regimen as compared to a prime-boost regimen. Complete protection is already observed after single administration of the recombinant adenoviral vectors hereof without booster administrations in the cotton rat model in the examples herein.

The invention is further described by the following illustrative examples. The examples do not limit the invention in any way. They merely serve to clarify the invention.

EXAMPLES

Example 1

Preparation of Adenoviral Vectors

Figure 15:
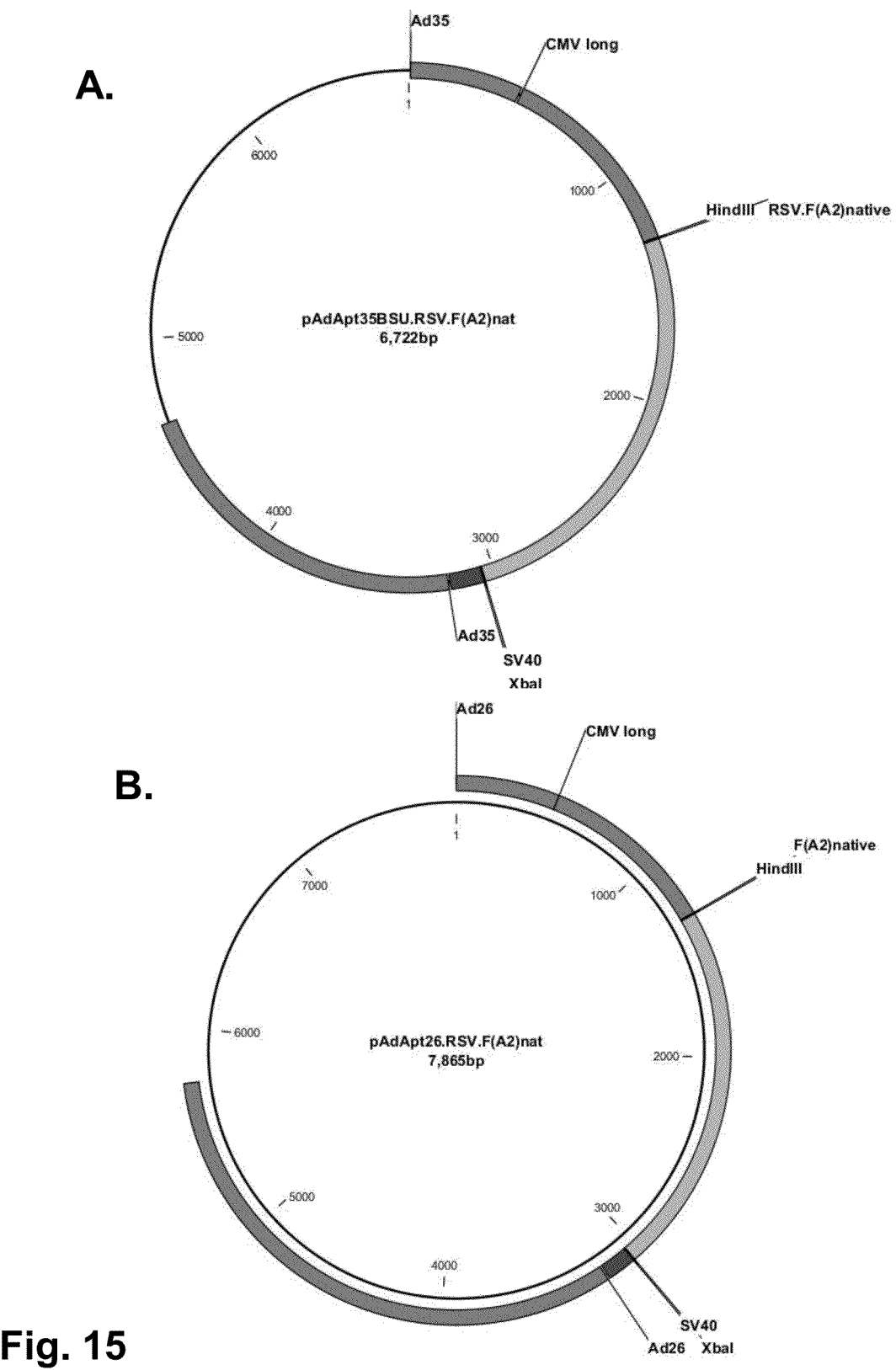
FIG. 15 shows maps of plasmids comprising the left end of the genome of Ad35 and Ad26 with the sequence encoding RSV F:
  A. pAdApt35BSU.RSV.F(A2)nat, and B. pAdApt26.RSV.F(A2)nat

Cloning RSV F gene into E1 region of Ad35 and Ad26:
The RSV.F(A2)nat gene, coding for the native RSV fusion (F) protein of the A2 strain (Genbank ACO83301.1), was gene optimized for human expression and synthesized, by Geneart. A Kozak sequence (5' GCCACC 3') was included directly in front of the ATG start codon, and two stop codons (5' TGA TAA 3') were added at the end of the RSV.F(A2)nat coding sequence. The RSV.F(A2)nat gene was inserted in the pAdApt35BSU plasmid and in the pAdApt26 plasmid via HindIII and XbaI sites. The resulting plasmids, pAdApt35BSU.RSV.F(A2)nat and pAdApt26.RSV.F(A2)nat are depicted in FIG. 15. The peptide of the F protein, and the codon optimized sequence encoding that peptide, are provided in Table 1 as SEQ. ID. NOs:1 and 2, respectively.

Cell Culture:
PER.C6® cells (Fallaux et al., 1998, *Hum Gene Ther* 9: 1909-1917) were maintained in Dulbecco's modified Eagle's medium (DMEM) with 10% fetal bovine serum (FBS), supplemented with 10 mM $MgCl_2$.

Adenovirus generation, infections and passaging:
All adenoviruses were generated in PER.C6® cells by single homologous recombination and produced as previously described (for rAd35: Havenga et al., 2006, *J. Gen. Virol.* 87: 2135-2143; for rAd26: Abbink et al., 2007, *J. Virol.* 81: 4654-4663). Briefly, PER.C6® cells were transfected with Ad vector plasmids, using Lipofectamine according to the instructions provided by the manufacturer (Life Technologies). For rescue of Ad35 vectors carrying the RSV.F (A2)nat transgene expression cassette, the pAdApt35BSU.RSV.F(A2)nat plasmid and pWE/Ad35.pIX-rITR.dE3.5orf6 cosmid were used, whereas for Ad26 vectors carrying the RSV.F(A2)nat transgene expression cassette, the pAdApt26.RSV.F(A2)nat plasmid and pWE.Ad26.dE3.5orf6.cosmid were used. Cells were harvested one day after full CPE, freeze-thawed, centrifuged for 5 min at 3,000 rpm, and stored at −20° C. Next the viruses were plaque purified and amplified in PER.C6® cultured on a single well of a multiwell 24 tissue culture plate. Further amplification was carried out in PER.C6® cultured using a T25 tissue culture flask and a T175 tissue culture flask. Of the T175 crude lysate, 3 to 5 ml was used to inoculate 20×T175 triple-layer tissue culture flasks containing 70% confluent layers of PER.C6® cells. The virus was purified using a two-step CsCl purification method. Finally, the virus was stored in aliquots at −85° C.

Example 2

Induction of Immunity Against RSV F Using Recombinant Adenovirus Serotypes 26 and 35 In Vivo This is an experiment to investigate the ability of the recombinant adenovirus serotype (Ad26) and recombinant adenovirus serotype 35 (Ad35) to induce immunity against the glycoprotein F antigen of RSV in BALB/c mice.

In this study animals were distributed in experimental groups of 5 mice. Animals were immunized with a single dose of Ad26 or Ad35 carrying the full-length RSV F gene (Ad26-RSV.F or Ad35-RSV.F) or no transgene (Ad26e or Ad35e). Three 10-fold serial dilutions of rAd ranging from $10^{10}$ to $10^8$ virus particles (vp) were given intramuscularly. As controls, one group of 3 animals received the empty vector Ad26e and one group received the empty vector Ad35e.

The ELISPOT assay is used to determine the relative number of F protein-specific IFNγ-secreting T cells in the spleen, and is essentially done as described by Radošević et al., (Clin Vaccine Immunol. 2010; 17(11):1687-94.). For the stimulation of splenocytes in the ELISPOT assay, two peptide pools consisting of 11-amino-acid-overlapping 15-mer peptides spanning the whole sequence of the RSV F (A2) protein was used. The numbers of spot-forming units (SFU) per $10^6$ cells were calculated.

For the determination of antibody titers an ELISA assay was used. For this, ELISA plates (Thermo Scientific) were coated with 25 µg/ml RSV Long whole inactivated antigen (Virion Serion, cat# BA113VS). Diluted serum samples were added to the plates, and IgG antibodies against RSV were determined using biotin-labeled anti-Mouse IgG (DAKO, cat# E0413), using detection by horseradish peroxidase (PO)-conjugated streptavidin (SA). Titers were calculated by linear interpolation, using 1.5×OD signal from 50× diluted naïve serum as cut-off. The titers of RSV-Specific IgG1 and IgG2a antibodies in the serum of the mouse was determined using PO-labeled anti-mouse IgG1 and PO-labeled anti-mouse IgG2a (Southern Biotechnology Associates, cat#s 1070-05 and 1080-05) were used to quantify subclasses.

Virus neutralizing activity (VNA) of the antibodies was determined by microneutralization assay, essentially done as described by Johnson et al. (J Infect Dis. 1999 July; 180(1): 35-40.). RSV-susceptible VERO cells were seeded in 96-well cell-culture plates one day prior to infection. On the day of infection, serial diluted sera and controls were mixed with 1200 pfu of RSV (Long or B1) and incubated 1 h at 37° C. Subsequently, virus/antibody mixes were transferred to 96-wells plates containing VERO cell monolayers. Three days later monolayers were fixed with 80% ice-cold acetone and RSV antigen was determined with an anti-F monoclonal antibody. The neutralizing titer is expressed as the serum dilution ($log_2$) that causes 50% reduction in the OD450 from virus-only control wells ($IC_{50}$).

At week 2 and week 8 post-prime animals were sacrificed and cellular and humoral responses were monitored as described above.

Figure 1A:
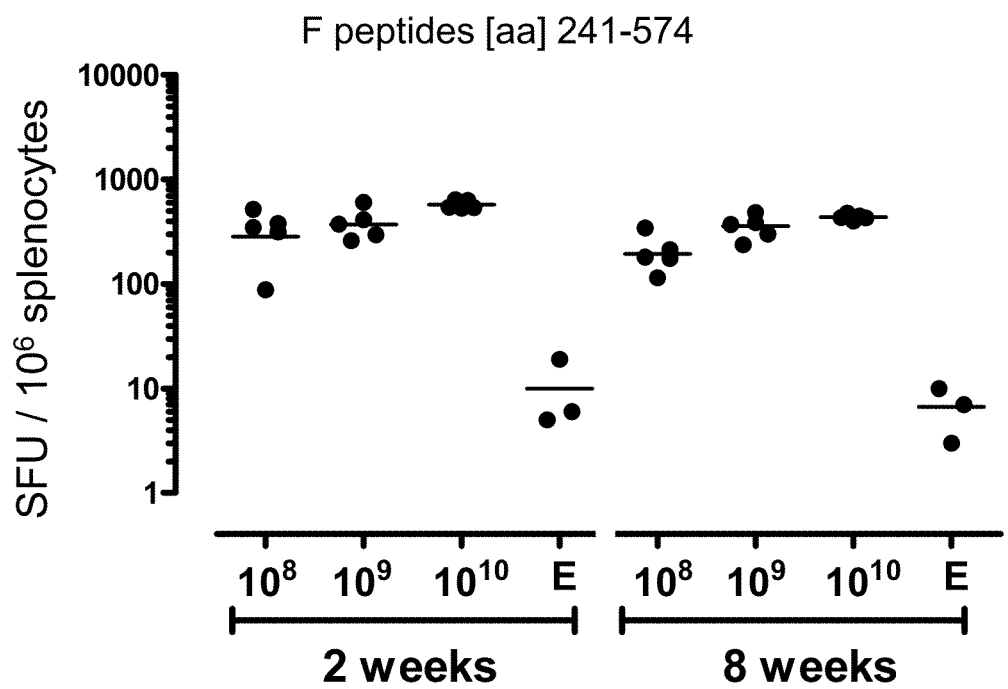
Figure 1B:
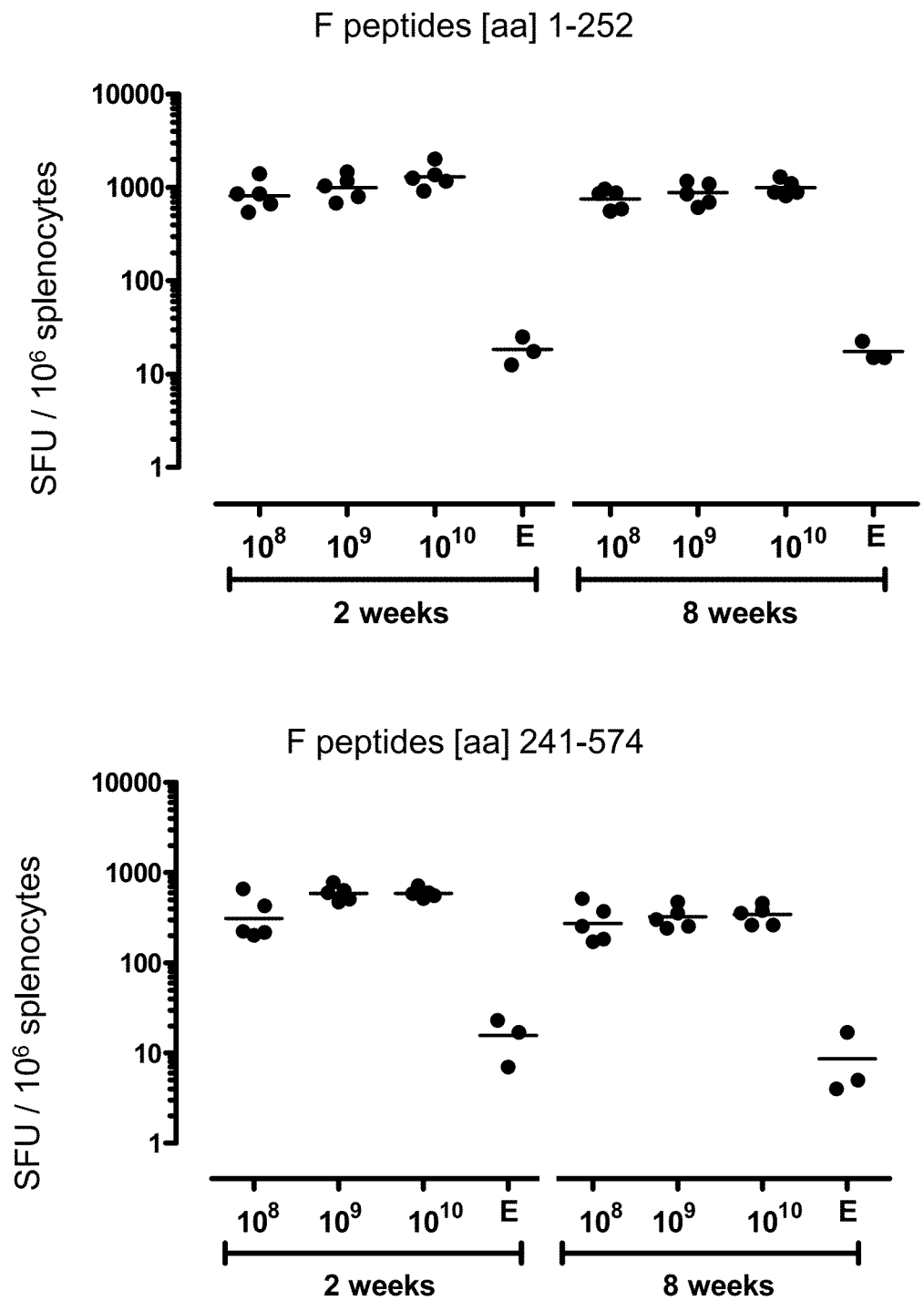

FIG. 1 shows that all doses of Ad26-RSV.F (FIG. 1A) and Ad35-RSV.F (FIG. 1B) were effective in inducing a good cellular immune responses and that the responses were stable over time. No significant differences of vector dose on T cell response with either Ad26-RSV.F or Ad35-RSV.F were observed.

Figure 2:
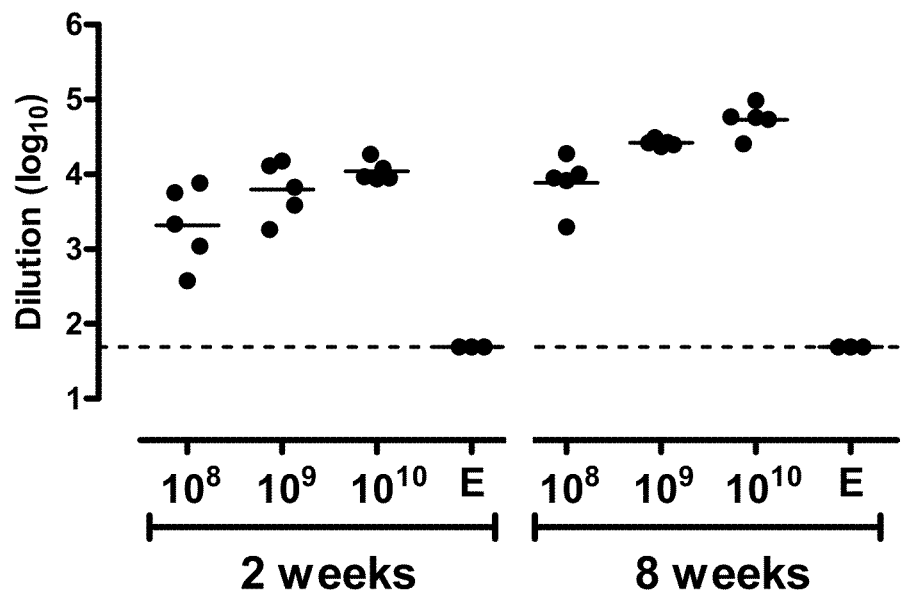
FIG. 2 shows the antibody response against RSV in mice upon immunization with different doses of rAd26 and rAd35 based vectors harboring the RSV F gene at 2 and 8 weeks after immunization.
Figure 2:
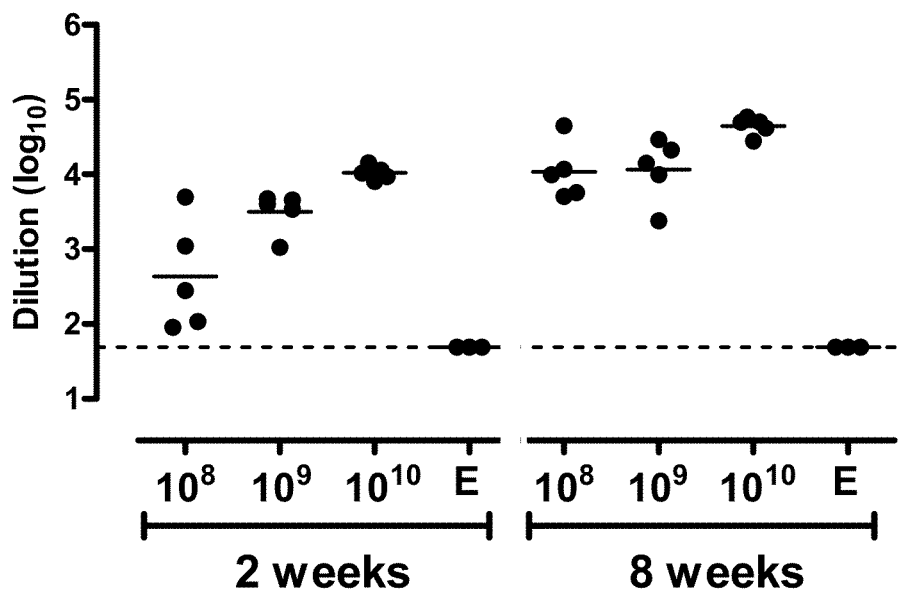

FIG. 2 shows the antibody titers in the same experiment as described above. Both vectors induced very clear time and dose-dependent increase in ELISA titers (FIG. 2). Anti-F titers clearly increase from 2 to 8 weeks, which was significant for the $10^{10}$ dose. At 8 weeks there was no difference in titers between the Ad26-RSV.F or Ad35-RSV.F vectors.

Figure 3:
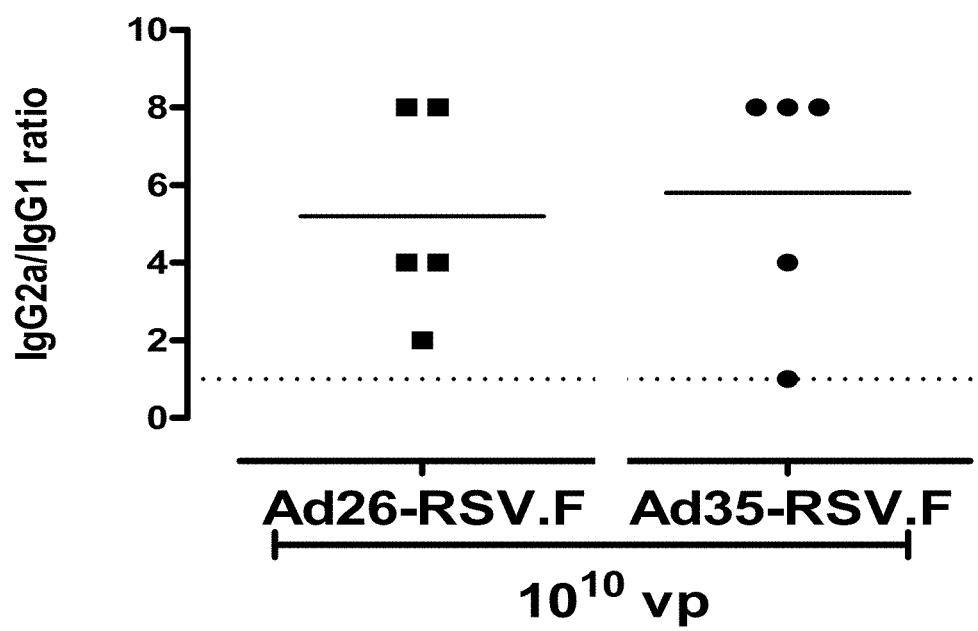
FIG. 3 shows the results of ratio of IgG2a vs. IgG 1 antibody response against RSV in mice upon immunization with $10^{10}$ vp of rAd26 and rAd35 based vectors harboring the RSV F gene at 8 weeks after immunization.

The subclass distribution (IgG1 vs IgG2a) of F-specific IgG was determined to evaluate the balance of Th1 vs Th2 response. A skewed Th2/Th1 response predispose animals to develop vaccine-enhanced RSV disease as seen with formalin-inactivated RSV. As shown in FIG. 3, the IgG2a/IgG1 ratio for both Ad26-RSV.F and Ad35-RSV.F is higher than 1. This strongly indicates that adenovectors Ad26-RSV.F and Ad35-RSV.F exhibit rather a Th1 type than a Th2 type of response.

Figure 4:
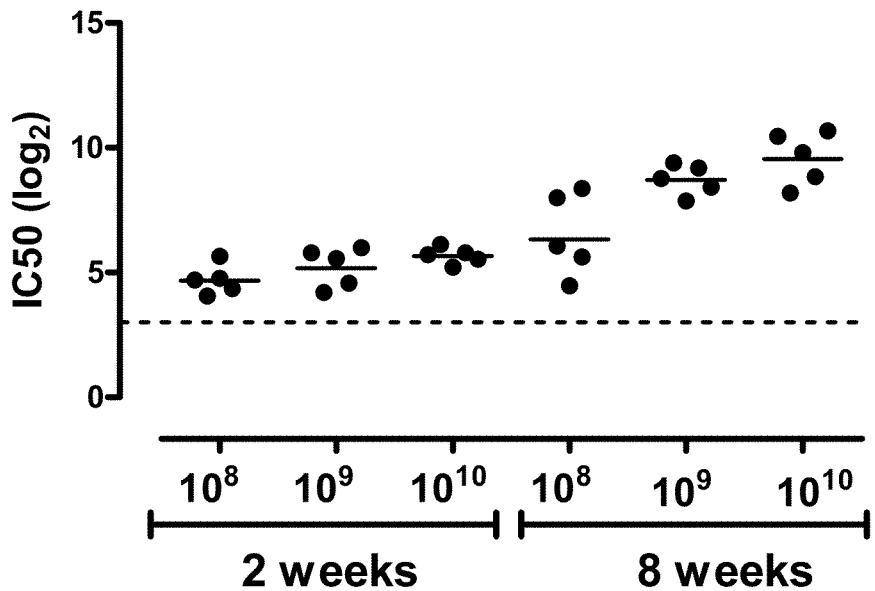
FIG. 4 shows the virus neutralization capacity against RSV Long in mice upon immunization with different doses of rAd26 (A) and rAd35 (B) based vectors harboring the RSV F gene at 2 and 8 weeks after immunization.
Figure 4:
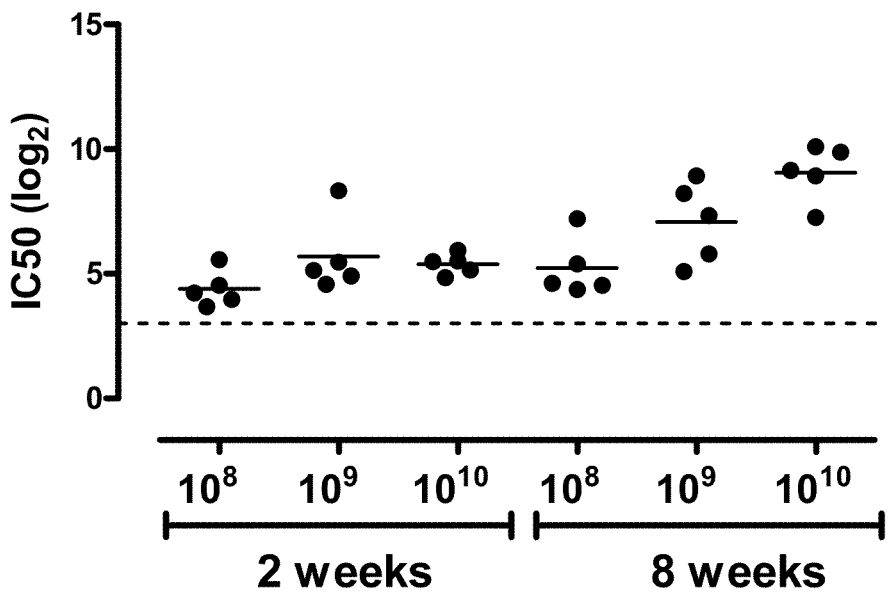

FIG. 4 shows the virus neutralizing titers (VNA) of the same sera used for the antibody titers. Immunization with Ad26-RSV.F and rAd35-RSV.F led to the induction of neutralizing antibody titers. VNA titers strongly increased between two and eight weeks post-prime in mice given $10^{10}$ vp. At eight weeks there was no difference in titers between Ad26-RSV.F and Ad35-RSV.F vectors in mice given $10^{10}$ vp.

From these immunization experiments it is evident that Ad35 and Ad26 vectors harboring the RSV.F transgene induce strong cellular and humoral responses against RSV.F.

Example 3

Immunity Against RSV.F after Heterologous Prime-Boost Using Recombinant Adenoviral Vectors Encoding RSV.F This study was designed to investigate the ability of prime-boost regimens based on adenoviral vectors derived from two different serotypes to induce immunity against RSV.F.

This study involved BALB/c mice distributed in experimental groups of 8 mice. Animals were immunized by intramuscular injection with $10^{10}$ vp carrying the wild type sequence of the RSV.F gene based on/derived from RSV A2 (Ad-RSV.F or Ad35-RSV.F) or no transgene (Ad26e or Ad35e). One group of animals was primed at week with Ad26-RSV.F and boosted at week 4 with Ad35-RSV.F or Ad35e. Another group of animals was primed with Ad35-RSV.F and boosted at week 4 with Ad26-RSV.F or Ad26e. A control group of mice was primed with Ad35e and boosted at week 4 with Ad26e. At week 6 and week 12 post prime 8 animals were sacrificed at each time point and cellular and humoral responses were monitored with immunological assays well known to persons skilled in the art and as described above.

Figure 5A:
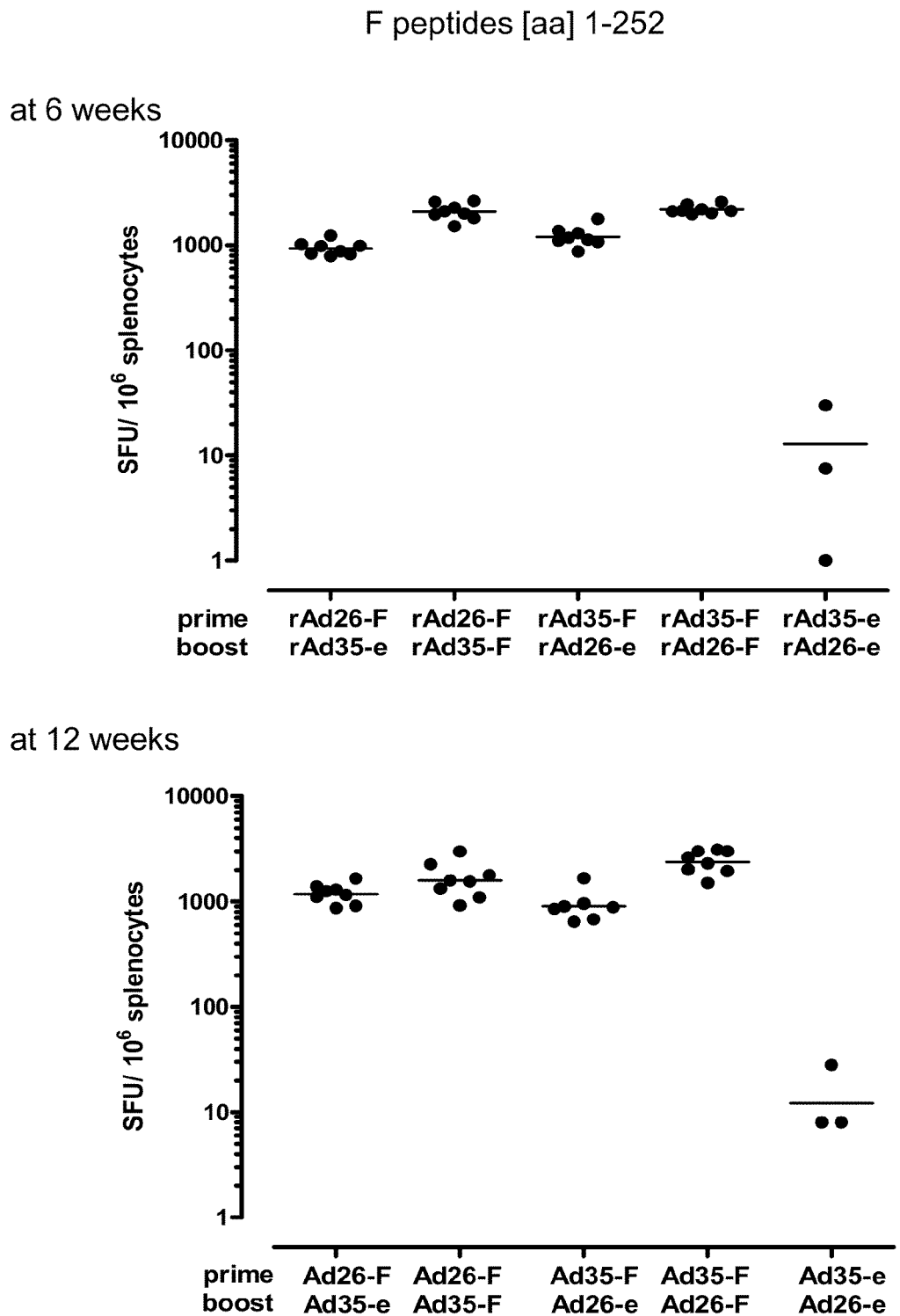
FIG. 5 shows the cellular immune response against (A) F peptides overlapping the aa 1-252 of F and (B) F peptides overlapping the aa 241-574 of F of mice upon prime boost immunization with rAd26 and rAd35 based vectors harboring the RSV F gene at 6 and 12 weeks after primary immunization.
Figure 5B:
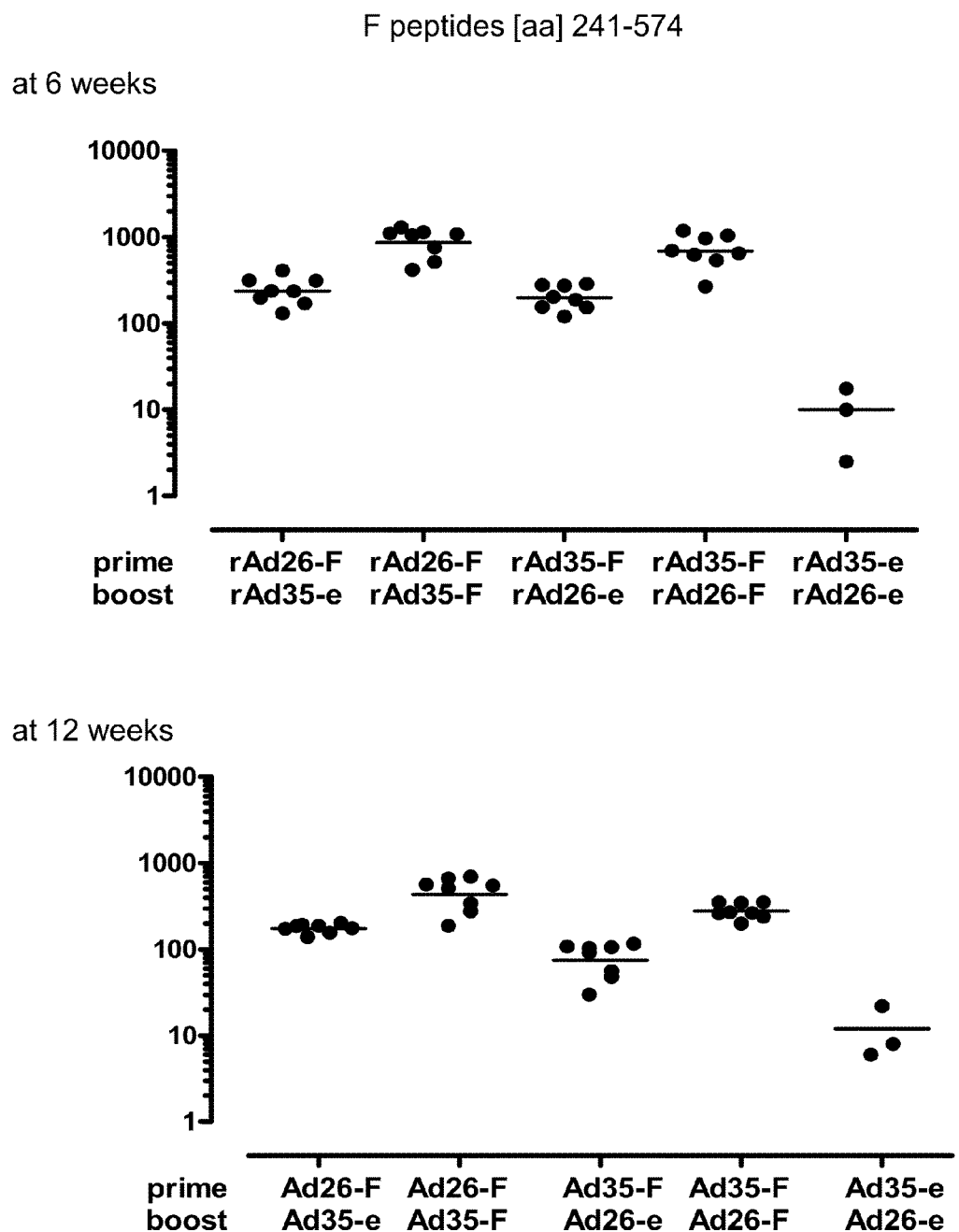

FIG. 5 shows the cellular response at 6 and 12 weeks after the first immunization. At 6 weeks after prime (and 2 weeks post-boost), a significant boost effect by both Ad26-RSV.F and Ad35-RSV.F on T cell responses was measured, and the magnitude of T cell response was independent of order of immunization with Ad26-RSV.F or Ad35-RSV.F in prime-boost. At 12 weeks after prime (8 weeks post-boost), mice primed with Ad26-RSV.F had maintained higher levels of F-specific T cells either in primed-only and prime-boosted animals, compared to rAd35-RSV.F primed animals. Overall, the numbers of F-specific lymphocytes (SFU) were high and stable for at least 12 weeks in all animals immunized with either rAd26-RSV.F or rAd35-RSV.F (prime/or prime-boost).

Figure 6:
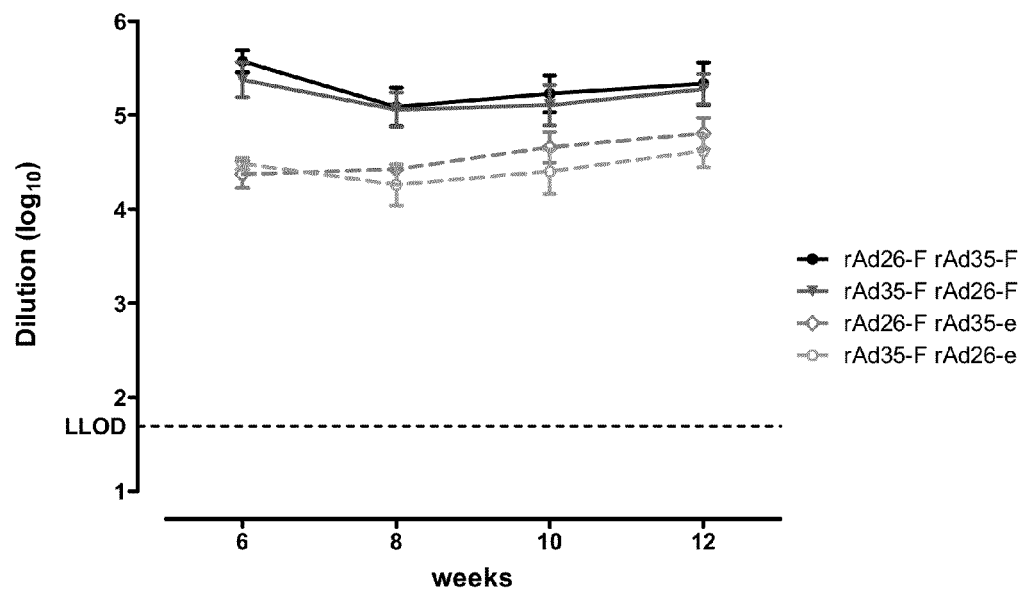
FIG. 6 shows the antibody response against RSV in mice upon prime boost immunization with rAd26 and rAd35 based vectors harboring the RSV F gene at different time points after the first immunization.

FIG. 6 shows the humoral response at different time points after prime-boost vaccination with the adenoviral vectors. Ad35.RSV.F and Ad26.RSV.F prime equally well, and a significant boost effect induced by either Ad26.RSV.F or rAd35.RSV.F on B cell responses was shown. Moreover, the magnitude of B cell responses in heterologous prime-boost was independent of the order of Ad35.RSV.F and Ad26.RSV.F immunization, and after boost ELISA titers remained stable for 12 weeks.

Figure 7:
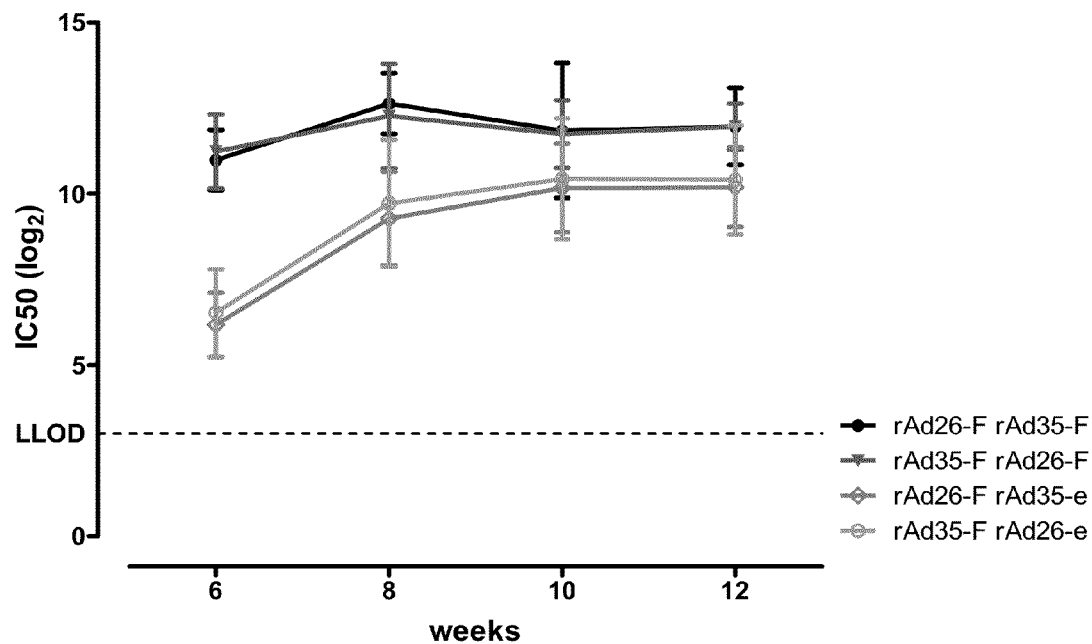
FIG. 7 shows the virus neutralization capacity against RSV Long in mice serum upon prime boost immunization with different doses of rAd26 and rAd35 based vectors harboring the RSV F gene at different time points after the first immunization.

FIG. 7 shows the virus neutralizing antibody titers at different time points after prime-boost immunization. Both Ad35.RSV.F and Ad26.RSV.F vectors primed equally well to achieve clear VNA titers, as was observed for ELISA titers. Also, the increase in VNA titers after heterologous prime-boost was independent of the order of Ad35.RSV.F and Ad26.RSV.F immunization. Boost effect by either Ad26.RSV.F or Ad35.RSV.F on VNA titers was significant at both time points and already maximal at 6 weeks. Groups that were only primed with Ad.RSV.F have increased VNA titers at 12 weeks compared to 6 weeks. The RSV F sequence in the adenoviral vector constructs is derived from the RSV A2 isolate. The neutralizing assay described in this application is based on RSV Long strain, belonging to RSV subgroup A, demonstrating that the antibodies induced by F (A2) are able to cross-neutralize a different RSV A strain subtype.

Figure 8:
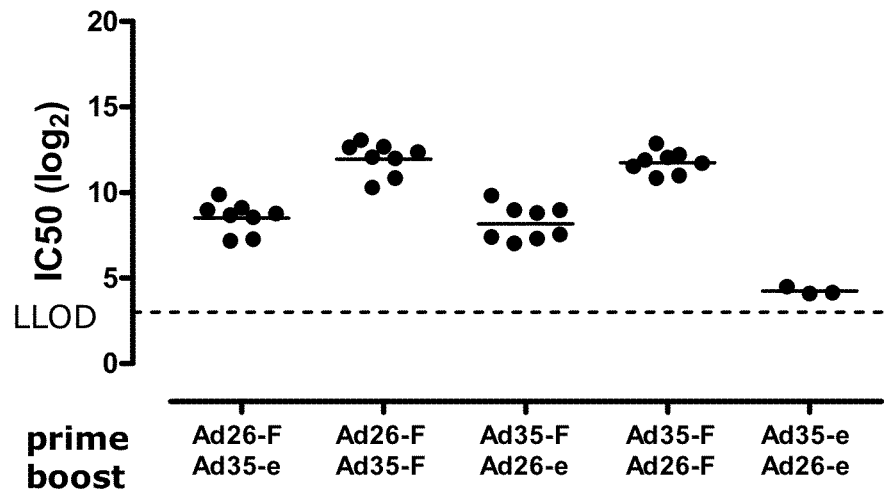
FIG. 8 shows the virus neutralization capacity against RSV B1 in mice upon prime boost immunization with different doses of rAd26 and rAd35 based vectors harboring the RSV F gene at different time points after the first immunization.
Figure 8:
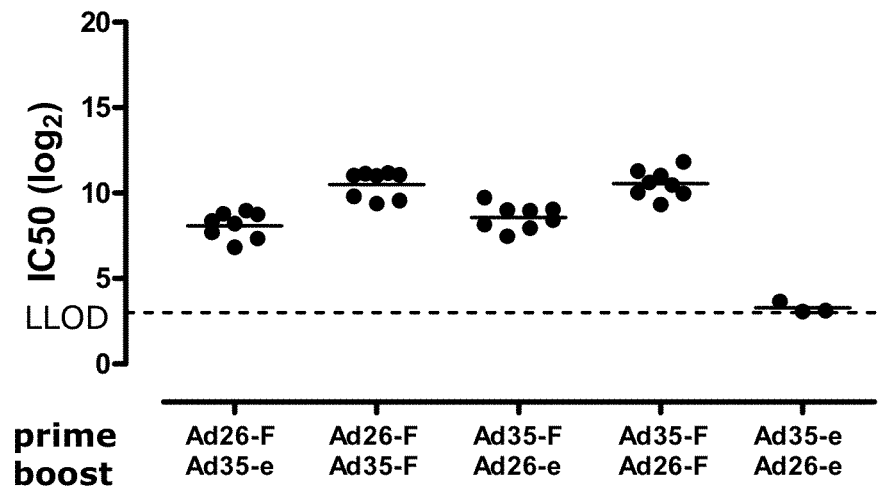

Because the RSV F protein is well conserved among RSV isolates, it was tested whether sera from animals immunized with Ad-RSV.F vectors were able to cross-neutralize a prototypical RSV B strain isolate, RSV B1. As shown in FIG. 8, sera of immunized mice were also capable of cross-neutralizing the B1 strain. The capacity to cross-neutralize RSV B1 was not dependent on which vector was used in prime-only groups, or order of prime-boost immunization with Ad26.RSV.F and Ad35.RSV.F vectors.

Collectively, these data show that in a prime-boost regimen, consecutive immunizations with Ad26.RSV.F and Ad35.RSV.F induce strong humoral and cellular responses, and that the humoral immune response includes the capacity to neutralize isolates of both RSV A and B subtypes.

Example 4

Inducing Protection Against RSV Infection Using Recombinant Adenoviral Vectors In Vivo in a Cotton Rat Model This experiment was performed to investigate the ability of prime-boost regimens based on adenoviral vectors derived from two different serotypes to induce protection against RSV challenge replication in the cotton rat. Cotton rats (*Sigmodon hispidus*) are susceptible to both upper and lower respiratory tract infection with RSV and were found to be at least 50-fold more permissive than mouse strains (Niewiesk et al., 2002, *Lab. Anim.* 36(4):357-72). Moreover, the cotton rat has been the primary model assessing the efficacy and safety of RSV candidate vaccines, antivirals and antibodies. Preclinical data generated in the cotton rat model advanced the development of two antibody formulations (RESPI-GAM® and SYNAGIS®) to clinical trials without the need of intermediate studies in non-human primates.

The study enrolled cotton rats in experimental groups of 8 cotton rats each. Animals were immunized by intramuscular injections of $10^9$ viral particles (vp) or $10^{10}$ vp adenoviral vectors carrying the full-length RSV F (A2) gene (Ad26.RSV.F or Ad35.RSV.F) or no transgene (Ad26e or Ad35e). Animals were boosted 28 days later with the same vp dose, either with the same vector (homologous prime-boost) or with other adenoviral serotype (heterologous prime-boost); control groups were immunized accordingly with Ad-e vectors, except that only 1 dose was applied ($10^{10}$). Control groups consisted of 6 animals. Animals infected intranasally with RSV A2 ($10^4$ plaque forming units (pfu)) were used as positive control for protection against challenge replication, as it is known that primary infection with RSV virus protects against secondary challenge replication (Prince. *Lab Invest* 1999, 79:1385-1392). Furthermore, formalin-inactivated RSV (FI-RSV) served as control for vaccine-enhanced histopathological disease. Three weeks after the second (boost) immunization, the cotton rats were challenged intranasally with $1\times10^5$ pfu of plaque-purified RSV A2. As controls, one group of cotton rats was not immunized but received challenge virus, and another control group was not immunized and not challenged. Cotton rats were sacrificed 5 days after infection, a time point at which RSV challenge virus reaches peak titers (Prince. *Lab Invest* 1999, 79:1385-1392), and lung and nose RSV titers were determined by virus plaque titration (Prince et al., 1978, *Am J Pathology* 93, 711-791).

Figure 9:
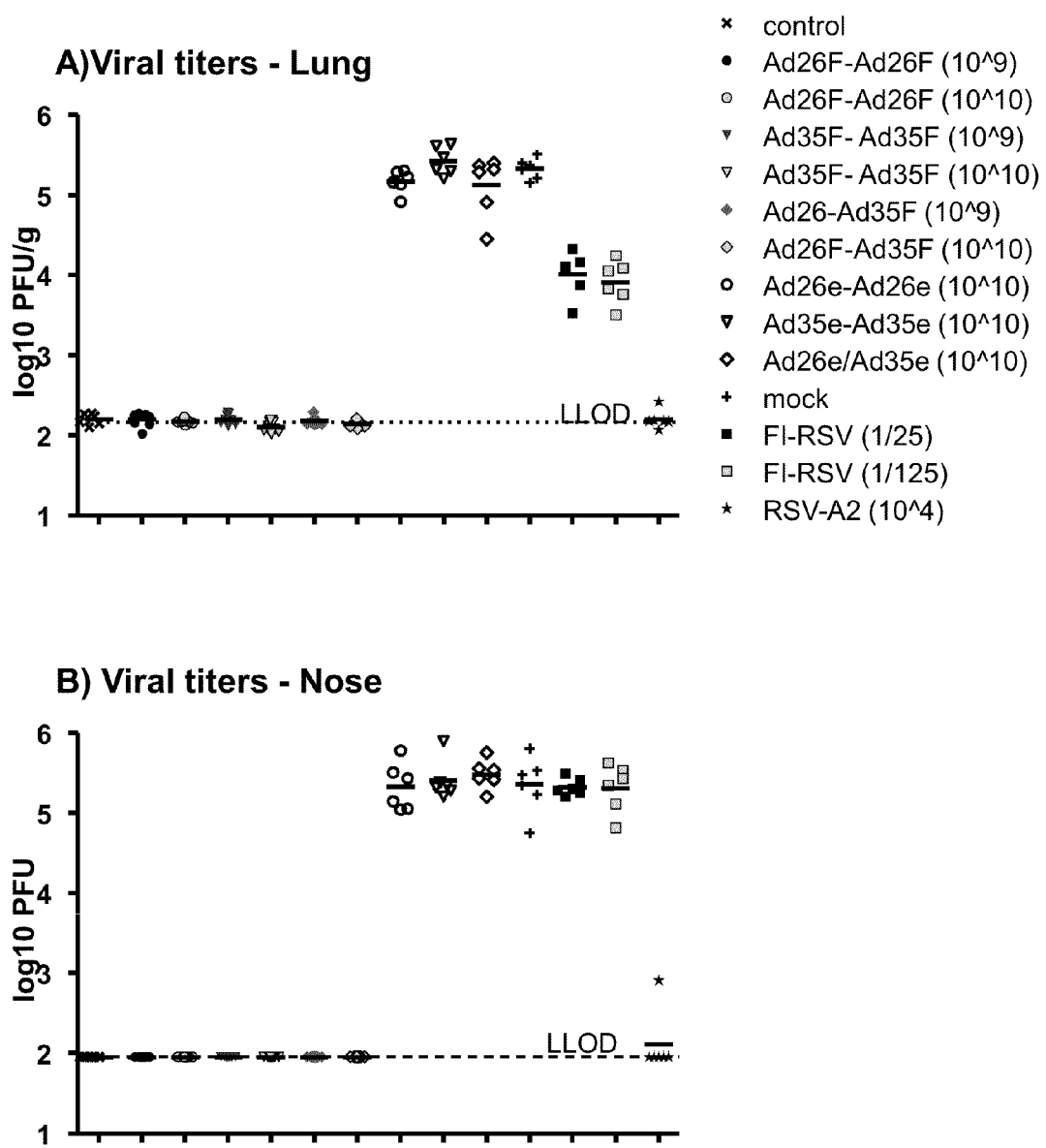
FIG. 9 shows the A) RSV lung titers and B) RSV nose titers in the cotton rats following prime boost immunization with different doses of rAd26 and rAd35 based vectors harboring the RSV F gene at 5 days post challenge.

FIG. 9 shows that high RSV virus titers in lungs and in nose were observed in non-immunized controls as well as animals receiving adenoviral vectors without transgene, respectively 5.3+/−0.13 $\log_{10}$ pfu/gram and 5.4+/−0.35 $\log_{10}$ pfu. In contrast, no challenge virus could be detected in lung and nose tissue from animals that received prime-boost immunization with Ad26.RSV.F and/or Ad35.RSV.F vectors, independent of dose or regimen.

These data clearly demonstrate that both Ad35-based and Ad26-based vectors give complete protection against RSV challenge replication in the cotton rat model. This was surprising, as Ad5 based adenoviral vectors encoding RSV F were known not to be capable of inducing complete protection in animal models after intramuscular administration.

In the course of the experiment, blood samples were taken before immunization (day 0), before the boost immunization (day 28), at day of challenge (day 49) and at day of sacrifice (day 54). The sera were tested in a plaque assay-based virus neutralization assay (VNA) for the induction of systemic RSV specific neutralizing antibodies as described by Prince (Prince et al., 1978, *Am J Pathology* 93, 711-791). The neutralizing titer is expressed as the serum dilution ($\log_2$) that causes 50% plaque reduction compared to from virus-only control wells ($IC_{50}$).

Figure 10:
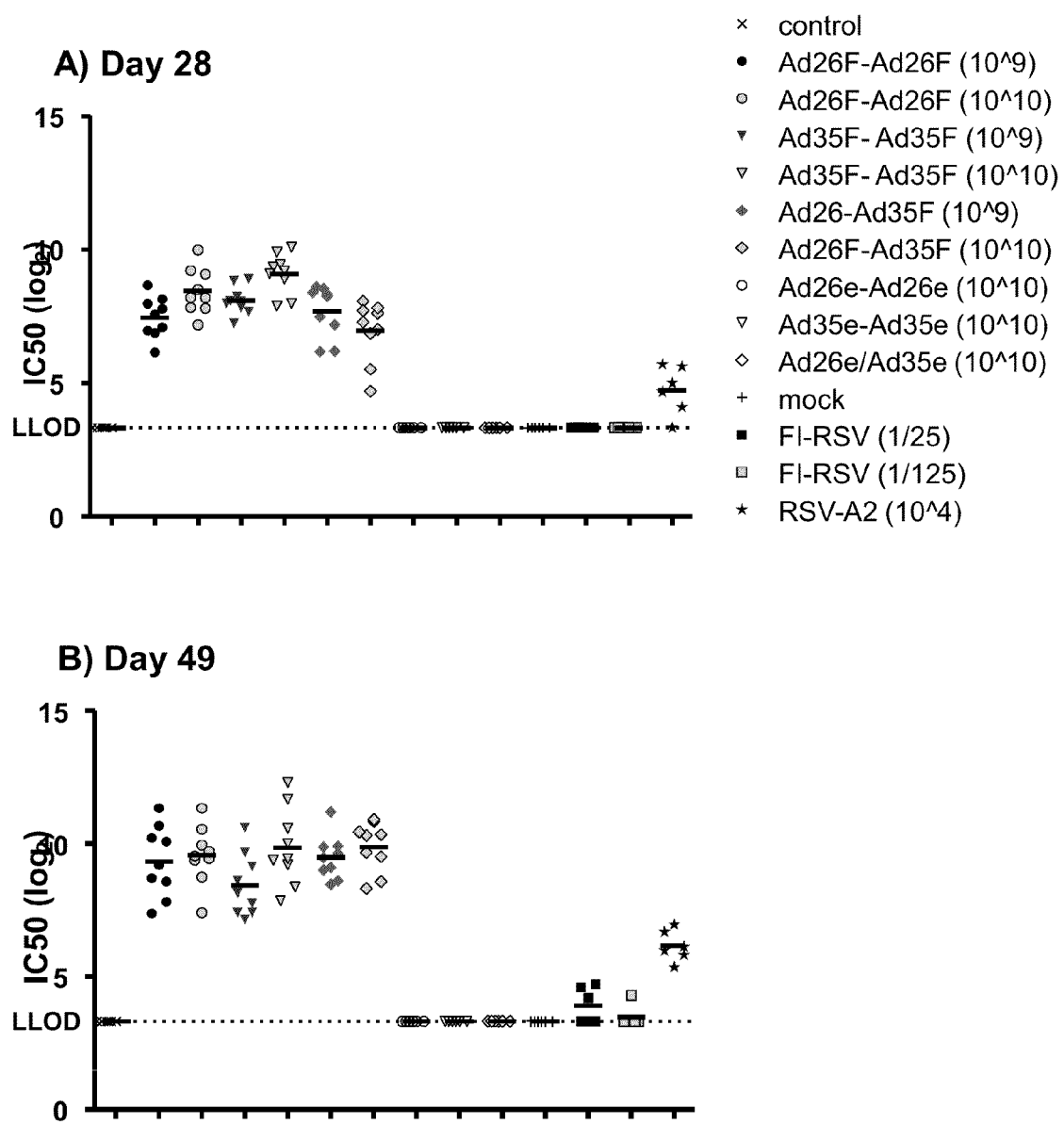
FIG. 10 shows the induction of virus neutralizing titers following prime boost immunization with different doses of rAd26 and rAd35 based vectors harboring the RSV F gene at A) 28 days, and B) 49 days after the first immunization.

FIG. 10 shows that control animals do not have virus neutralizing antibodies at day 28 and day 49, while high VNA titers are induced after animals were primed with Ad26.RSV.F or Ad35.RSV.F vectors. A moderate increase in VNA titer is observed after boost immunizations. Primary infection with RSV A2 virus resulted in rather moderate VNA titers that gradually increased in time.

Figure 11:
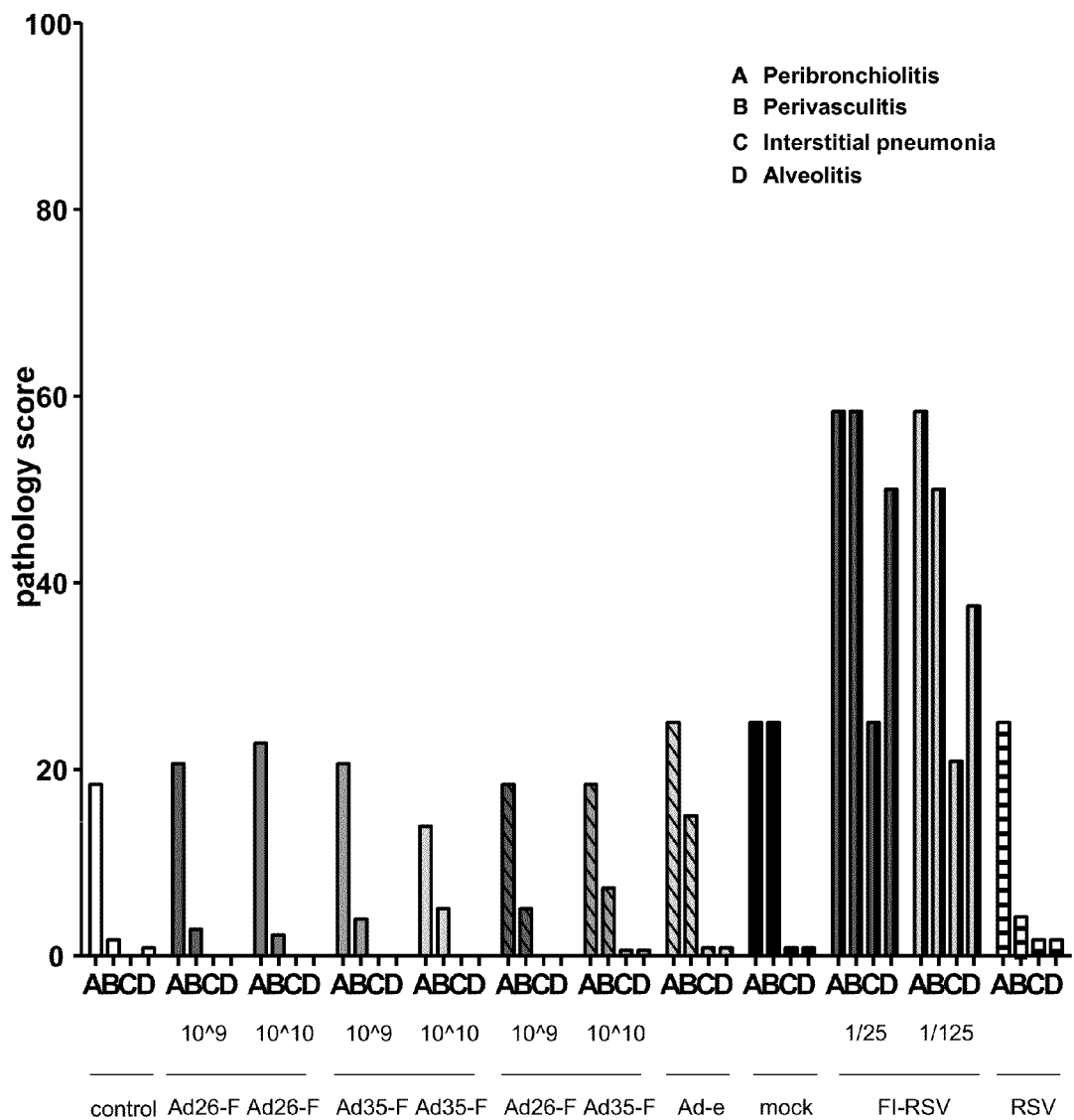
FIG. 11 shows the histopathological examination of the cotton rat lungs at day of sacrifice following prime boost immunization with different doses of rAd26 and rAd35 based vectors harboring the RSV F gene.

To evaluate whether Ad26.RSV.F or Ad35.RSV.F vaccine might exacerbate disease following a challenge with RSV A2, histopathological analyses of the lungs were performed 5 days after infection. The lungs were harvested, perfused with formalin, sectioned, and stained with hematoxylin and eosin for histologic examination. Histopathology score was done blinded, according to criteria published by Prince (Prince et al. *Lab Invest* 1999, 79:1385-1392), and scored for the following parameters: peribronchiolitis, perivasculitis, interstitial pneumonitis, and alveolitis. FIG. 11 shows the scoring of lung pathology of this experiment. Following RSV challenge, FI-RSV immunized animals showed elevated histopathology on all histopathology parameters examined, compared to mock-immunized challenged animals, which was expected based on earlier published studies (Prince et al. *Lab Invest* 1999, 79:1385-1392). Histopathology scores in Ad26.RSV.F and Ad35.RSV.F immunized compared to rAd-e or mock immunized animals, were similar, although perivasculitis in the rAd-RSV.F immunized animals appeared to be slightly lower. Thus, the Ad26.RSV.F and Ad35.RSV.F vaccines did not result in enhanced disease, unlike FI-RSV vaccines.

All vaccination strategies resulted in complete protection against RSV challenge replication, induced strong virus neutralizing antibodies, and enhanced pathology was not observed.

Example 5

Protective Efficacy of rAd Vectors Using Different Administration Routes after Single Immunization This study is to investigate the influence of administration routes on the protective efficacy induced by Ad26 or Ad35 vectors encoding RSV.F. The vaccine was either administered intramuscularly or intranasally.

Cotton rats that had received a single immunization with $1\times10^9$ or $1\times10^{10}$ viral particles (vp) of Ad26 or Ad35 carrying either the RSV F as transgene (Ad26.RSV.F or Ad35.RSV.F) or no transgene (Ad26-e or Ad35-e) at day 0, were challenged at day 49 with $10^5$ RSV pfu and sacrificed at day 54.

Figure 12:
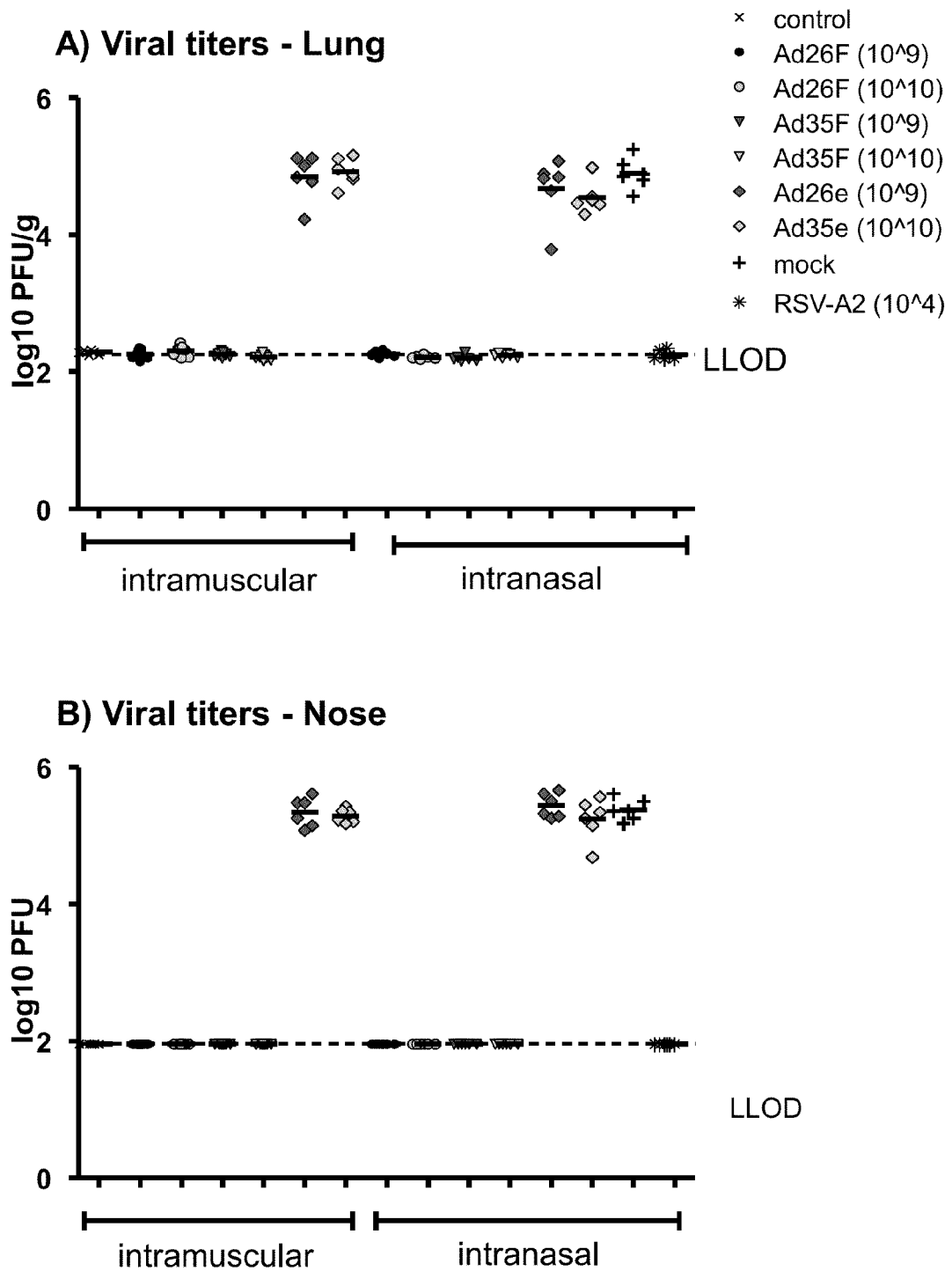
FIG. 12 shows A) the RSV lung titers and B) the RSV nose titers in the cotton rats following single dose immunization with different doses of rAd26 and rAd35 based vectors harboring the RSV F gene at 5 days post challenge, administered via different routes.

FIG. 12 shows the results of the experiments wherein the lung and nasal challenge virus were determined. High RSV virus titers were detected in lungs and noses from rats that were non-immunized or immunized with adenoviral vectors without a transgene, respectively, 4.9+/−0.22 $\log_{10}$ pfu/gram and 5.4+/−0.16 $\log_{10}$ pfu. In contrast, lungs and noses from animals that received either Ad35-RSV.F or Ad26-RSV.F were devoid of replicating challenge virus, independent of administration route and dose.

These data surprisingly demonstrate that each of Ad26- and Ad35-based vectors encoding RSV F protein provide complete protection in cotton rat challenge experiments, independent of the route of administration of the vectors. This was unexpected, since none of the published adenovirus-based RSV vaccines, which were based on other serotypes, had demonstrated complete protection after intramuscular vaccination.

Figure 13:
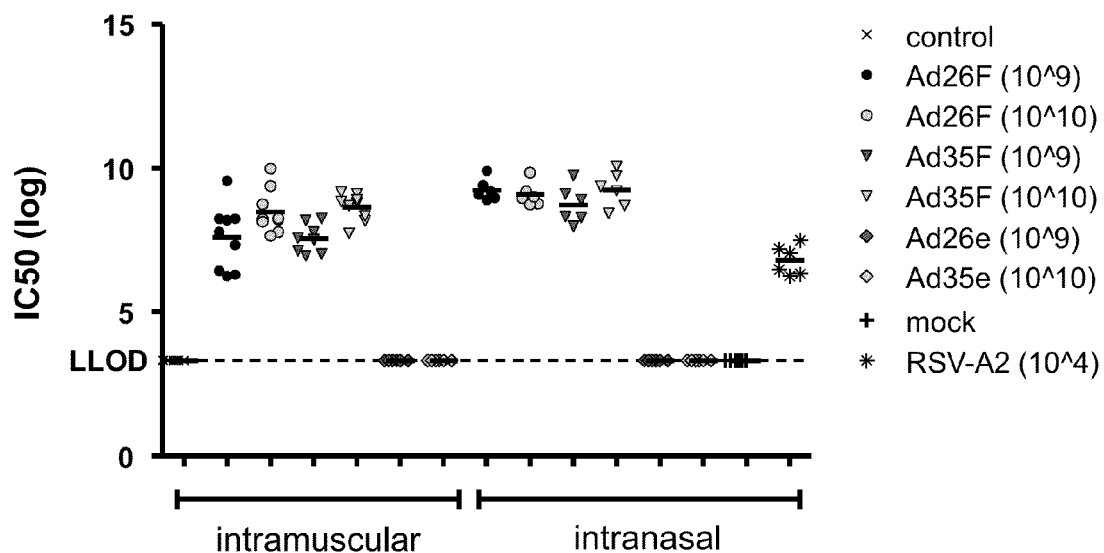
FIG. 13 shows the induced virus neutralizing titers following single dose immunization with different doses of rAd26 and rAd35 based vectors harboring the RSV F gene at 28 and 49 days after the first immunization, administered via different routes.
Figure 13:
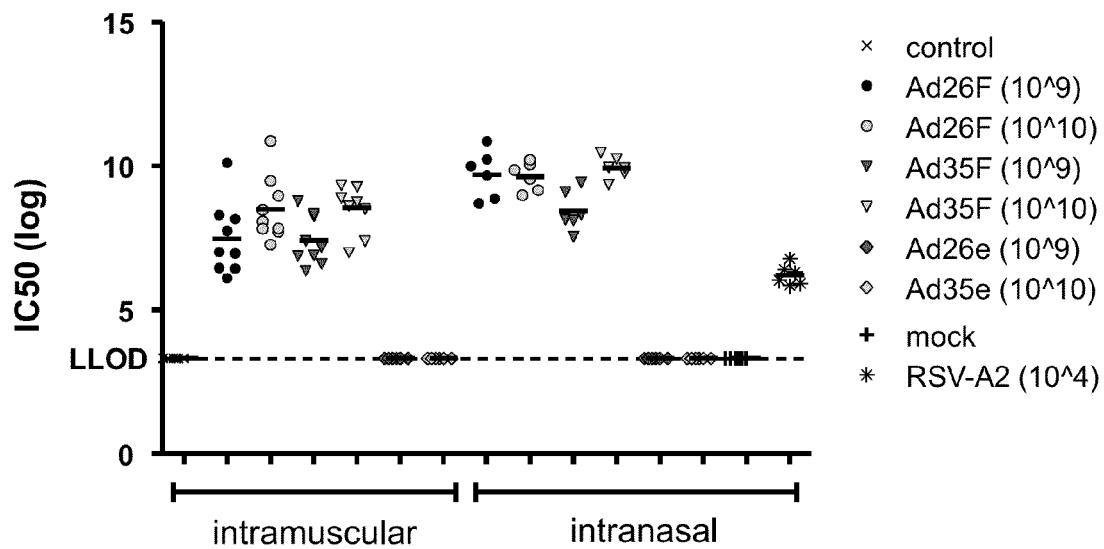

During the experiment, blood samples were taken before immunization (day 0), 4 weeks after immunization (day 28), and at day of challenge (day 49). The sera were tested in a neutralization test for the induction of RSV specific antibodies (FIG. 13). Prior to immunization no virus neutralizing antibodies were detected in any cotton rat. All adenoviral vector immunization strategies, independent of route of administration, clearly induced high VNA titers, which remained stable over time. These data surprisingly demonstrate that each of Ad26- and Ad35-based vectors encoding RSV F protein provide high titers of virus neutralizing antibodies in cotton rat immunization experiments, independent of the route of administration of the vectors.

Figure 14:
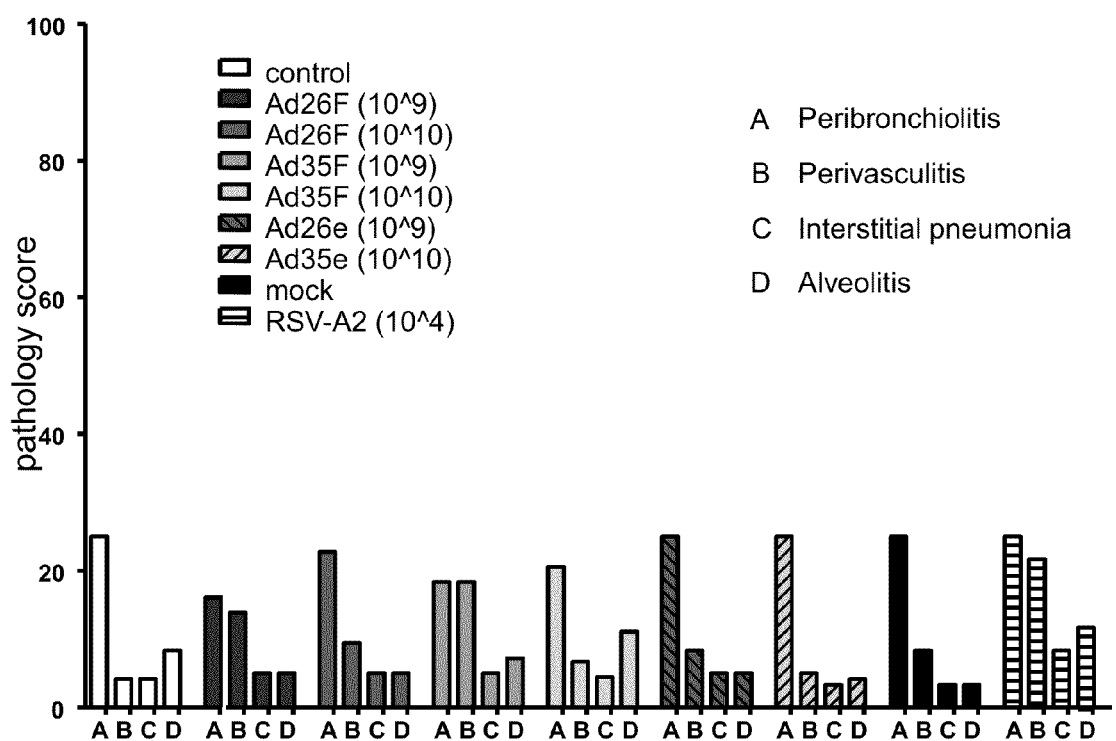
FIG. 14 shows the histopathological examination of the cotton rat lungs at day of sacrifice following single dose immunization (i.m.) with different doses of rAd26 and rAd35 based vectors harboring the RSV F gene at day of sacrifice.

To evaluate whether a single immunization of Ad26.RSV.F or Ad35.RSV.F vaccine can cause vaccine-enhanced disease following challenge with RSV A2, histopathological analyses of the lungs were performed 5 days after infection (FIG. 14). Single immunization with rAd26.RSV.F or rAd35.RSV.F resulted in similar immunopathology scores in rAd26.RSV.F or rAd35.RSV.F immunized compared to rAd-e or mock immunized animals, as observed in the prime-boost immunization experiments described above. Clearly, exacerbated disease was not observed, in contrast to animals that were primed with FI-RSV. Histopathology scores of animals immunized with rAd vectors were comparable to mock infected animals.

In conclusion, all single dose vaccination strategies resulted in complete protection against RSV challenge replication, induced strong virus neutralizing antibodies and did not show enhanced pathology.

Example 6

Vectors with Variants Such as Fragments of RSV for with Alternative Promoters Show Similar Immunogenicity The above examples have been conducted with vectors expressing the wild type RSV F. Other, truncated or modified forms of F have been constructed in rAd35, providing embodiments of fragments of RSV F in adenoviral vectors. These truncated or modified forms of F include a truncated form of RSV-F wherein the cytoplasmic domain and transmembrane region were lacking (i.e., only the ectodomain fragment remained), and a fragment form of RSV-F with truncation of cytoplasmic domain and transmembrane region and a further internal deletion in the ectodomain and addition of a trimerization domain. These vectors did not improve the responses over rAd35.RSV.F with full-length F protein.

In addition, other rAd35 vectors with different alternative promoters driving the expression of wild type RSV F, have been constructed.

Immunogencity of the modified forms of RSV. F and the promoter variants have been compared in the mouse model and compared to Ad35.RSV.F which express wild type F. All Ad35 vectors harboring these F variants or promoter variants showed responses in the same order of magnitude as Ad35.RSV.F.

Example 7

Figure 16:
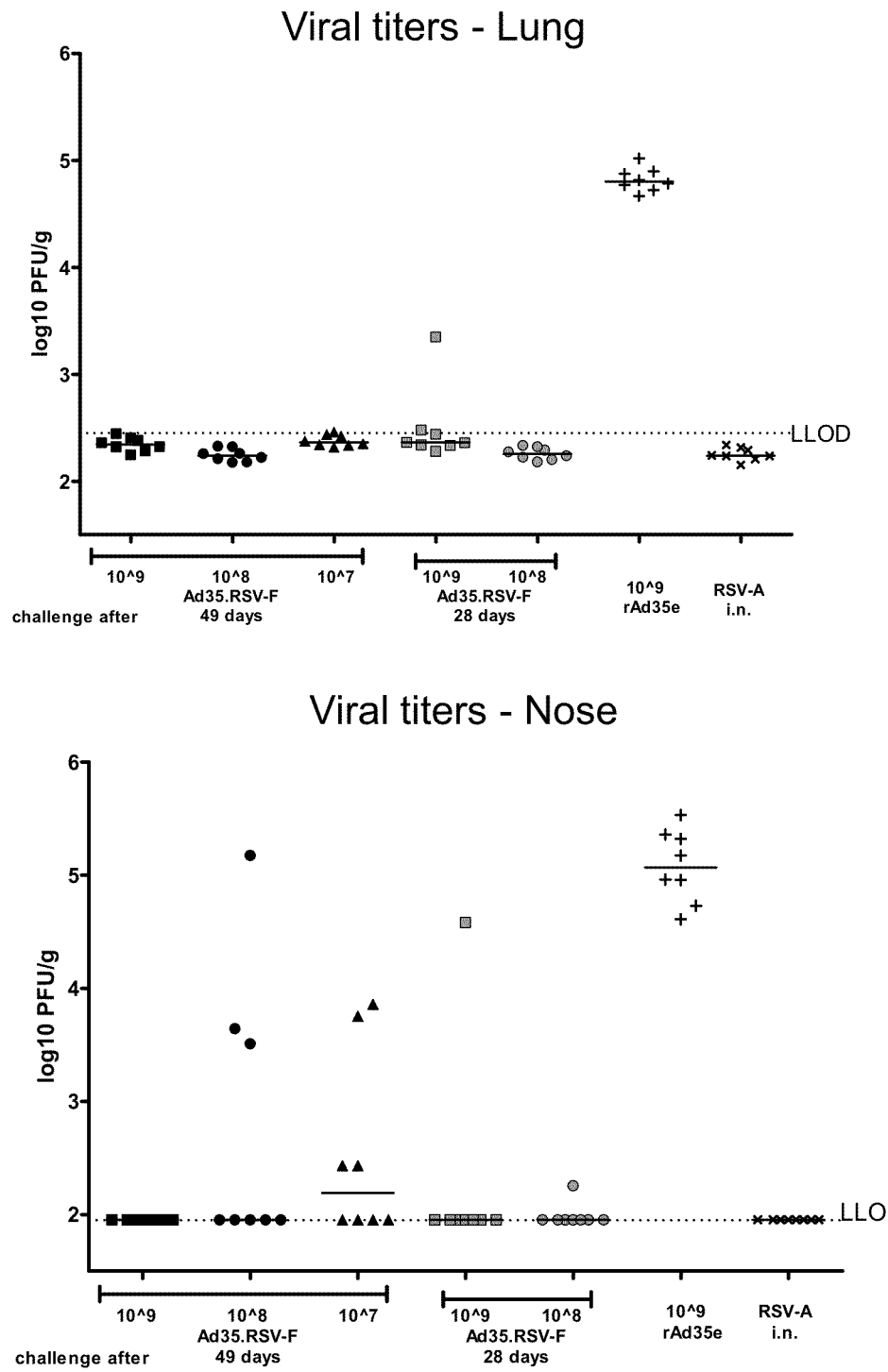
FIG. 16 shows A) the RSV lung titers and B) the RSV nose titers in the cotton rats following single dose immunization at day 0 or day 21 with different doses of rAd35 based vectors harboring the RSV F gene. Challenge was at day 49 and sacrifice at day 54.
Figure 17:
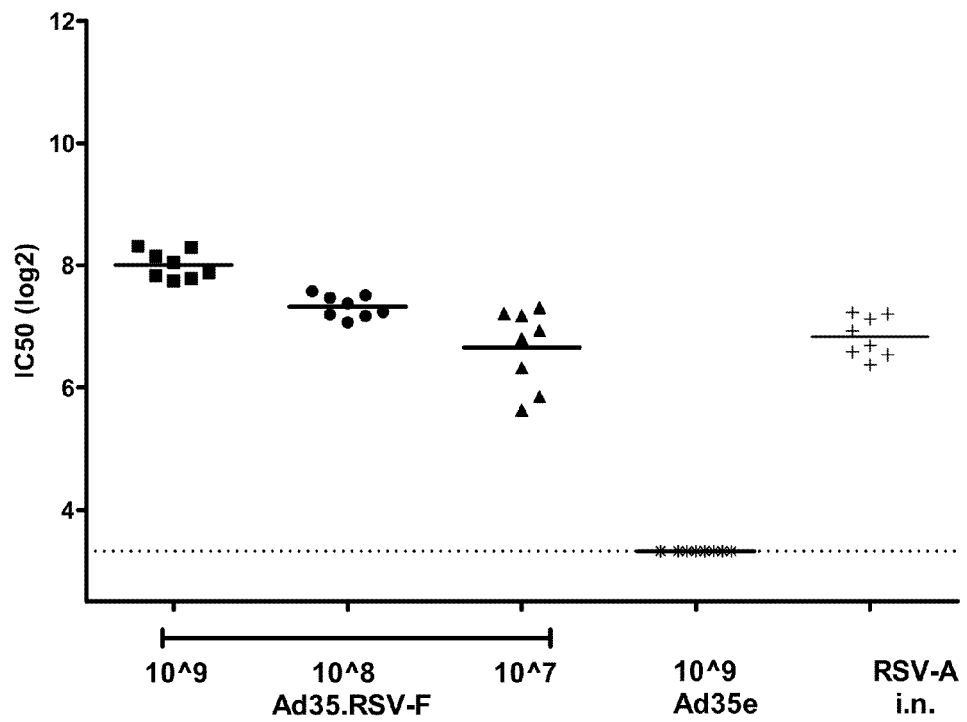
FIG. 17 shows the induction of virus neutralizing titers following single dose immunization with different doses of rAd35 harboring the RSV F gene at 49 days after immunization as described for FIG. 16.
Figure 18:
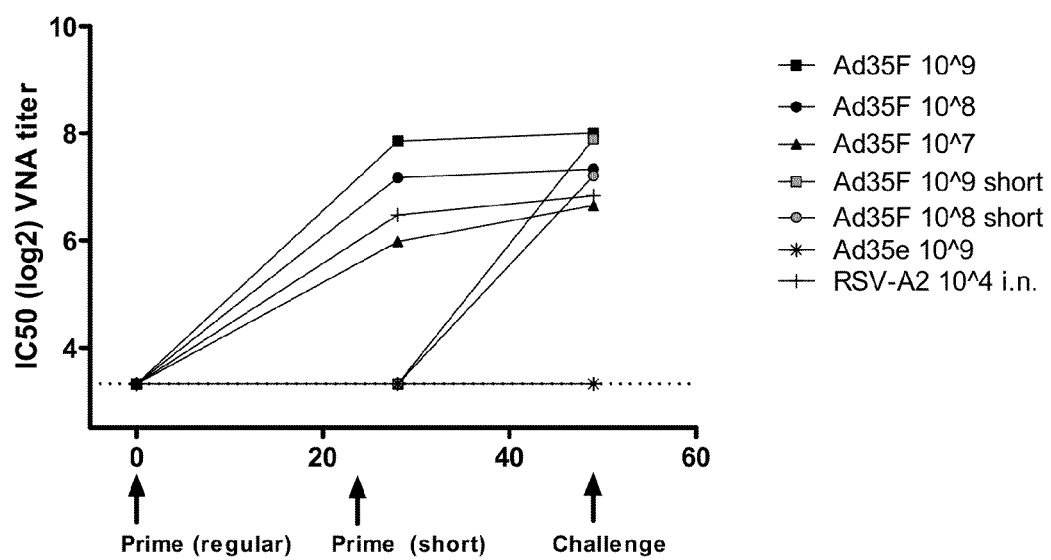
FIG. 18 shows the induction of virus neutralizing titers following single dose immunization with different doses of rAd35 harboring the RSV F gene during time after immunization

Short Term Protection Against RSV Infection after Recombinant Adenoviral Vectors Immunization In Vivo in a Cotton Rat Model This experiment determines the potential of rapid onset of protection by adenoviral vectors expressing the RSV-F protein in the cotton rat model. To this aim cotton rats in experimental groups of 8 cotton rats each were immunized by single intramuscular injection of $10^7$, $10^8$ or $10^9$ viral particles (vp) adenoviral vectors carrying the full-length RSV F (A2) gene (Ad35.RSV.F) or no transgene (Ad26e) at day 0 or at day 21. Animals infected intranasally with RSV A2 ($10^4$ plaque forming units (pfu)) were used as positive control for protection against challenge replication, as it is known that primary infection with RSV virus protects against secondary challenge replication (Prince. *Lab Invest* 1999, 79:1385-1392). At day 49, seven or four weeks after immunization, the cotton rats were challenged intranasally with $1 \times 10^5$ pfu of plaque-purified RSV A2. Cotton rats were sacrificed 5 days after infection, a time point at which RSV challenge virus reaches peak titers (Prince. *Lab Invest* 1999, 79:1385-1392), and lung and nose RSV titers were determined by virus plaque titration (Prince et al., 1978, *Am J Pathology* 93, 711-791). FIG. 16 shows that high RSV virus titers in lungs and in nose were observed in animals receiving adenoviral vectors without transgene, respectively 4.8+/−0.11 $\log_{10}$ pfu/gram and 5.1+/− 0.32 $\log_{10}$ pfu/g. In contrast, all animals that received immunization with at high dose ($10^9$ vp) Ad35.RSV.F vectors were completely protected against RSV titers in the lungs and nose 7 weeks post immunization and almost completely protected 4 weeks post immunization. Lower doses of Ad35.RSV.F vectors conferred complete protection against RSV titers in the lungs and partial protection against nose titers at 4 and 7 weeks post immunization. Blood samples were taken at day of challenge (day 49). The sera were tested in a neutralization test for the induction of RSV specific antibodies (FIG. 17). Immunization with Ad vectors induced dose dependent VNA titers. FIG. 18 shows that control animals do not have virus neutralizing antibodies during the experiments, while high VNA titers are induced in animals 28 or 49 days after immunization with $10^7$ to $10^9$ Ad35.RSV.F vp. Prior to immunization no virus neutralizing antibodies were detected in any cotton rat. Immunization with adenoviral vectors induced dose dependent VNA titers that were higher or comparable to neutralizing titers generated by primary i.n. RSV infection. This experiment clearly indicates the rapid onset of protection against challenge virus replication by the Ad35 expressing RSV-F.

Example 8

Figure 19:
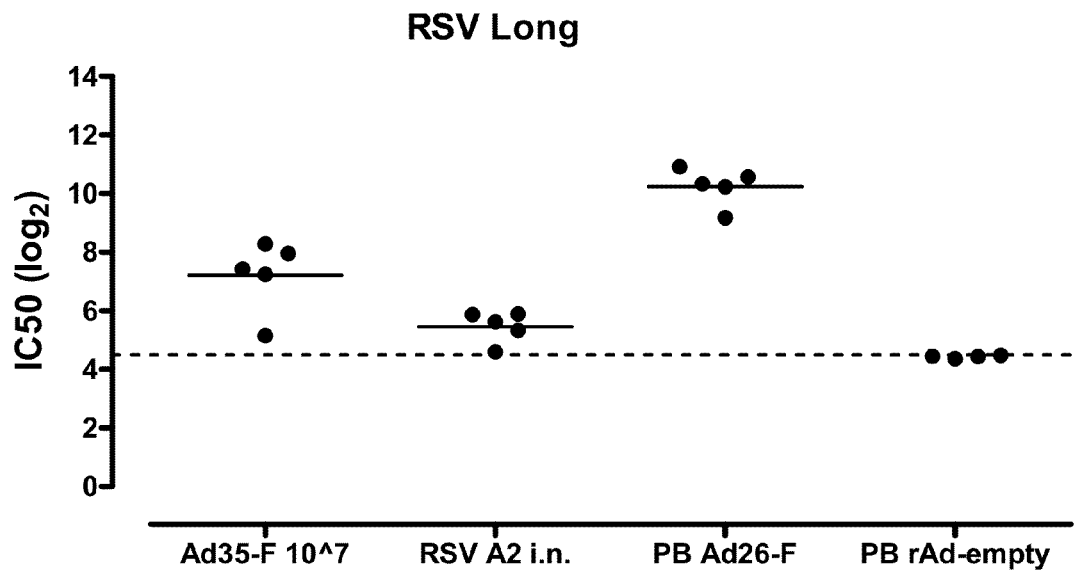
FIG. 19 shows the VNA titers 49 days after against RSV Long and RSV Bwash with serum derived from cotton rats immunized with a single dose of $10^{10}$ of Ad-35RSV F or no transgene (Ad-e). PB: prime boost.
Figure 19:
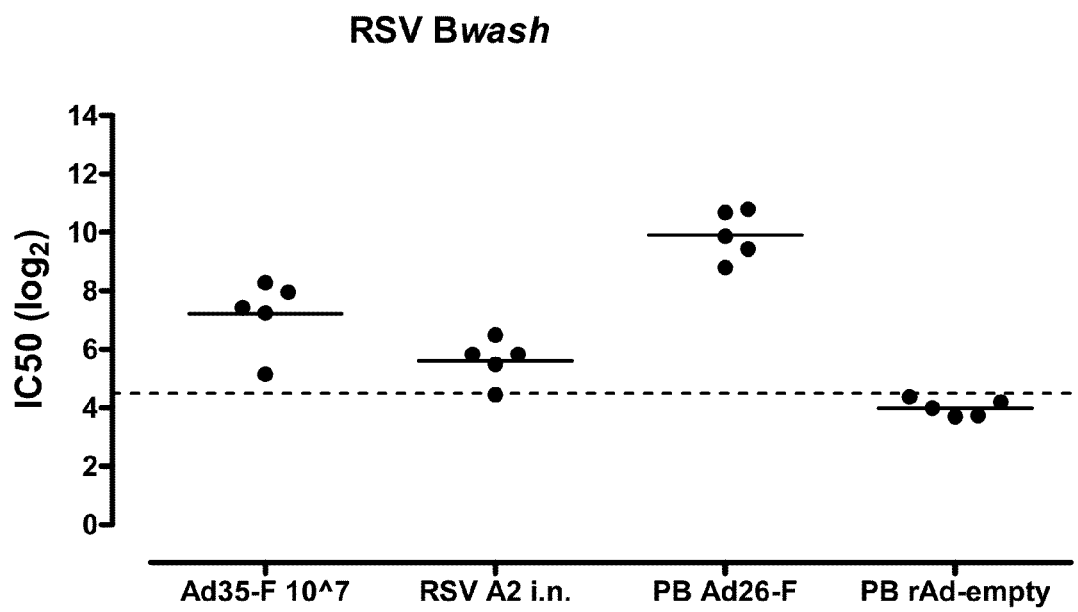

Protection Against RSV Subgroup a and Subgroup B Infection after Recombinant Adenoviral Vectors Immunization In Vivo in a Cotton Rat Model RSV strains can be divided in two subgroup, the A and B subgroups. This subtyping is based on differences in the antigenicity of the highly variable G glycoprotein. The sequence of the F protein is highly conserved but can also be classified in the same A and B subgroups. Patent application 0200 EO POO described that sera of Ad-RSV.F vectors immunized mice were also capable of cross-neutralizing the B1 strain in vitro. FIG. 19 clearly shows that cotton rat serum derived from cotton rats immunized with Ad35.RSV-$F_{A2}$ shows high VNA titers at day 49 post immunization against RSV Long (subgroup A) and Bwash (subgroup B, ATCC #1540). The in vivo protection against either subgroup A or B challenge was determined in the cotton rat using low adenovirusvector doses at $10^7$ and $10^8$ vp. To this aim cotton rats were divided in experimental groups of 8 cotton rats each. Animals were immunized at day 0 by intramuscular injections of $10^7$ or $10^8$ viral particles (vp) adenoviral vectors carrying the full-length RSV F (A2) gene (Ad35.RSV.F) or no transgene (Ad26e) at day 0. Animals infected intranasally with RSV A2 ($10^4$ plaque forming units (pfu)) were used as positive control for protection against challenge replication. At day 49 animals were i.n. challenged with either $10^5$ pfu RSV-A2, a RSV-A subgroup or RSV-B 15/97, a RSV-B strain.

Figure 20:
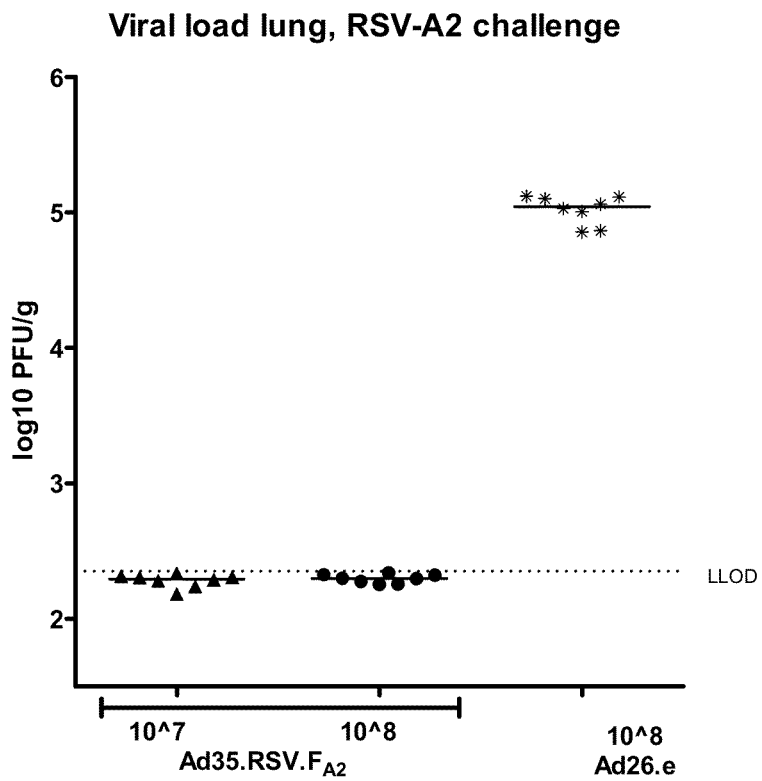
FIG. 20 shows the RSV lung titers in the cotton rats following single dose immunization at day 0 with different doses of rAd35 based vectors harboring the RSV F gene at 5 days post challenge with RSV A2 or RSV B15/97.
Figure 20:
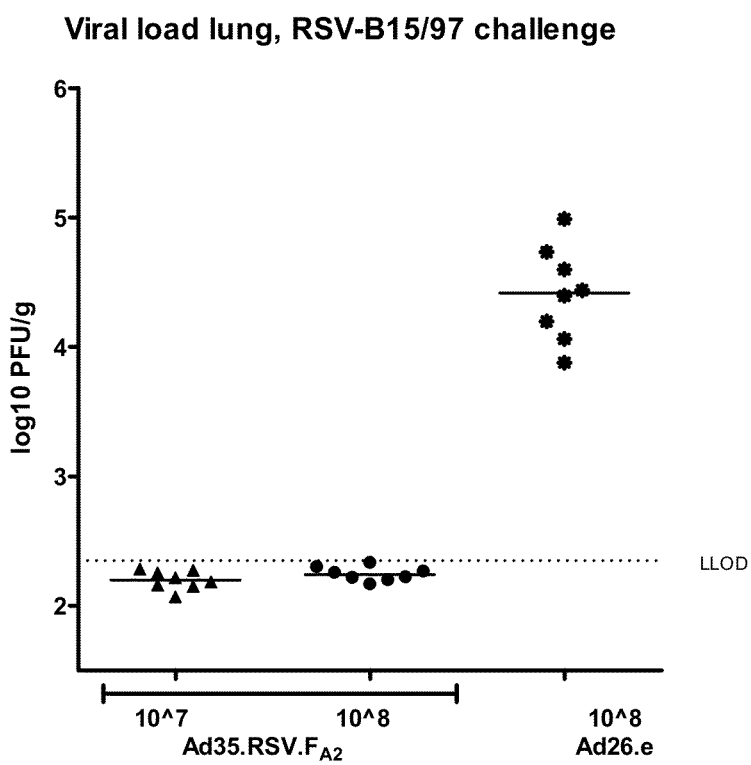
Figure 21:
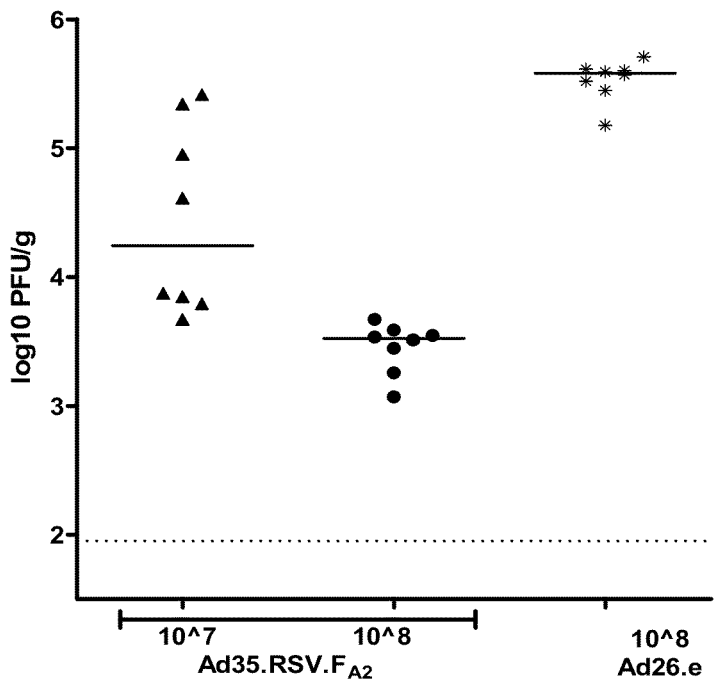
FIG. 21 shows the RSV nose titers in the cotton rats following single dose immunization at day 0 with different doses of rAd26 based vectors harboring the RSV F gene at 5 days post challenge with RSV A2 or RSV B15/97.
Figure 21:
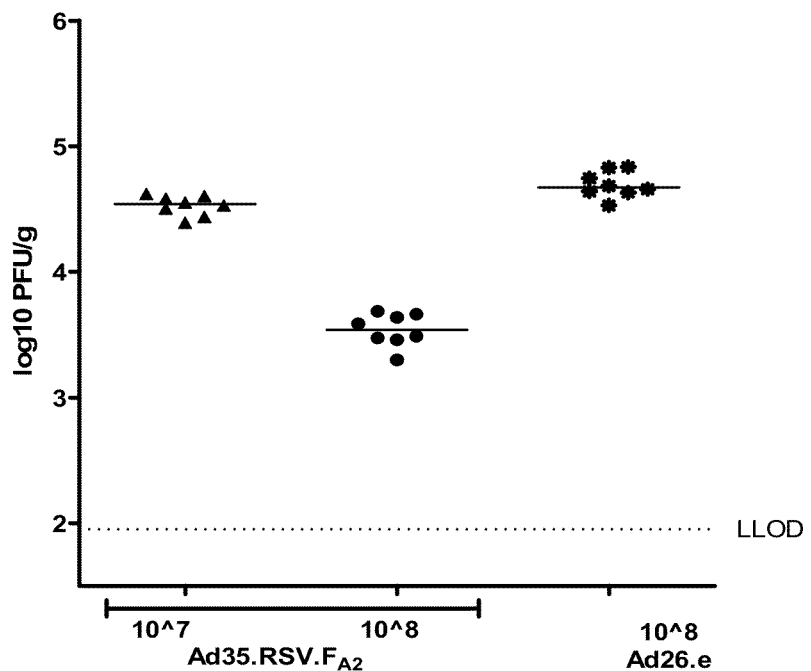
Figure 22:
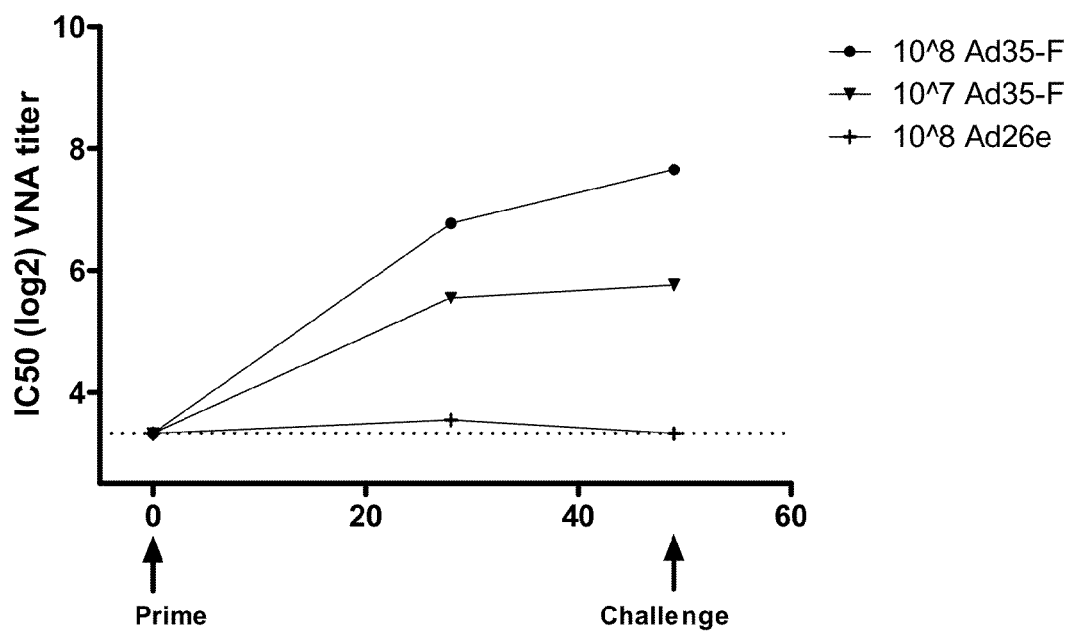
FIG. 22 shows the VNA titers the cotton rats serum following single dose immunization at day 0 with different doses of rAd35 based vectors harboring the RSV F gene during time after immunization.

FIG. 20 shows that high RSV virus titers in lungs were observed in animals receiving adenoviral vectors without transgene. In contrast, no challenge virus could be detected in lung and nose tissue from animals that received immunization with Ad35.RSV.F vectors. No differences were observed on protection when challenged with either RSV-A2 or RSV-B 15/97. Ad35.RSV.$F_{A2}$ showed complete protection against lung challenge replication at $10^7$ and $10^8$ vp FIG. 21 shows that high RSV virus titers in nose were observed in animals receiving adenoviral vectors without transgene. Ad35.RSV.$F_{A2}$ showed partial protection against nose challenge virus replication at $10^8$ vp. No differences were observed on protection when challenged with either RSV-A2 or RSV-B 15/97. During the experiment, blood samples were taken at day 28 and at day of challenge (day 49). The sera were tested in a neutralization test for the induction of RSV specific antibodies. FIG. 22 shows the virus neutralization titers during time course of the experiment and shows that control animals do not have virus neutralizing antibodies during the experiments. High VNA titers are induced in animals 28 days after immunization with $10^8$ or $10^7$ Ad35.RSV.F vp.

Example 9

Figure 23:
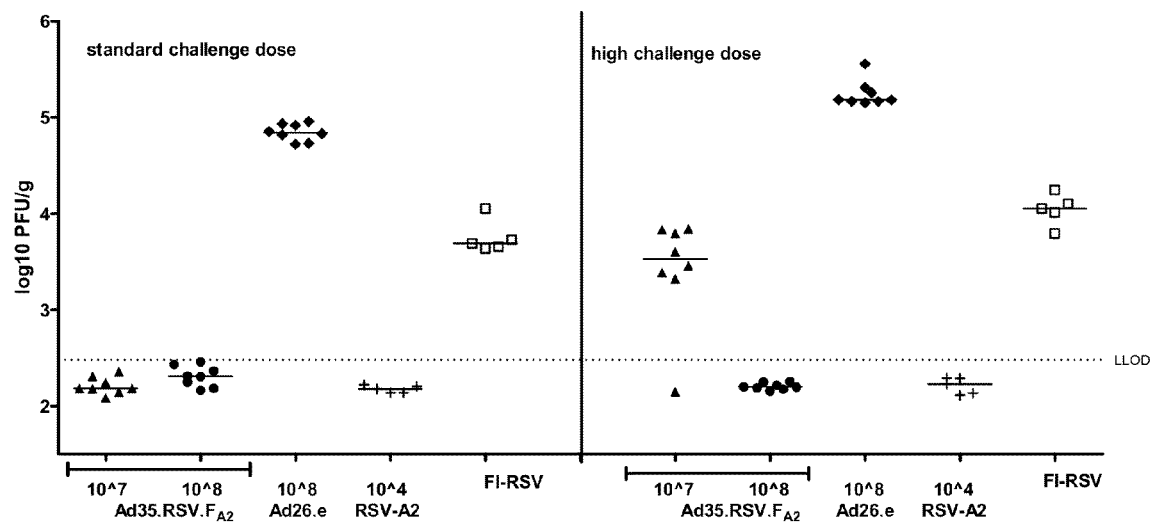
FIG. 23 shows the RSV lung titers in the cotton rats following single dose immunization at day 0 with different doses of rAd35 based vectors harboring the RSV F gene at 5 days post challenge with a standard dose ($10^5$) or a high dose ($5 \times 10^5$) of RSV A2.
Figure 24:
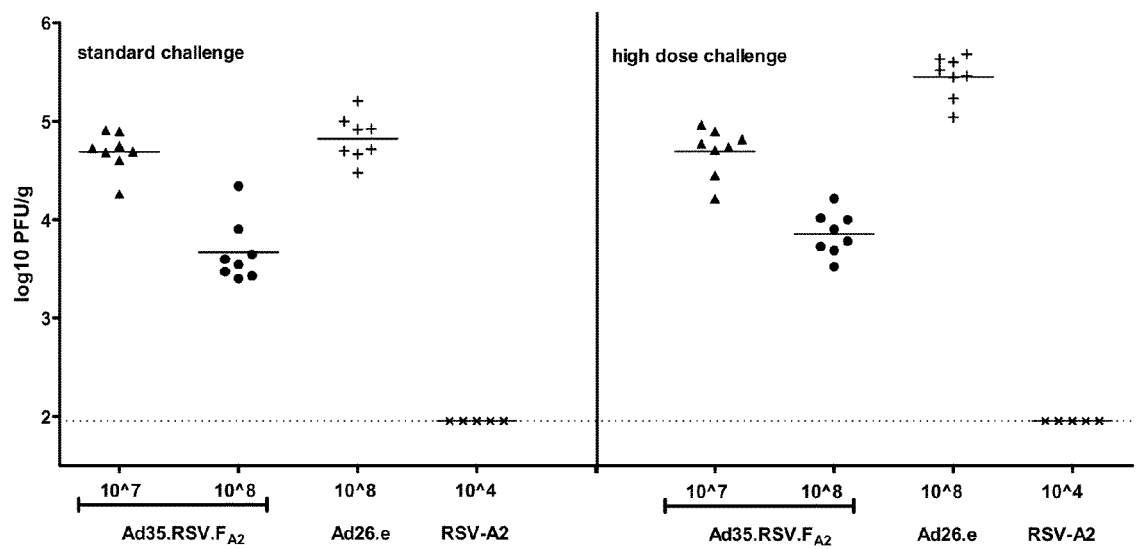
FIG. 24 shows the RSV nose titers in the cotton rats following single dose immunization at day 0 with different doses of rAd35 based vectors harboring the RSV F gene at 5 days post challenge with challenge with a standard dose ($10^5$) or a high dose ($5 \times 10^5$) of RSV A2.

Protection Against a High Challenge Dose of RSV-A2 after Recombinant Adenoviral Vectors Immunization In Vivo in a Cotton Rat Model This example determines the protection against a high challenge dose of $5 \times 10^5$ pfu compared to the standard dose of $1 \times 10^5$ pfu RSV-A2. The study enrolled cotton rats in experimental groups of 8 cotton rats each. Animals were immunized by intramuscular injections of low doses of $10^7$ or $10^8$ viral particles (vp) adenoviral vectors carrying the full-length RSV F (A2) gene (Ad35.RSV.F) or no transgene (Ad26e) at day 0. Animals infected intranasally with RSV A2 ($10^4$ plaque forming units (pfu)) were used as positive control for protection against challenge replication. Cotton rats were sacrificed 5 days after infection, and lung and nose RSV titers were determined by virus plaque titration. FIG. 23 shows that higher challenge dose induces higher lung viral load in animals receiving adenoviral vectors without transgene than with the standard challenge dose. Animals that received an immunization with $10^8$ vp Ad35.RSV.F vectors were complete protected in the lung against standard and high RSV challenge titers. FIG. 24 shows that animals that received a immunization with $10^8$ or $10^7$ vp Ad35.RSV.F vectors were partially protected in the nose against standard and high RSV challenge titers.

Example 10

Figure 25:
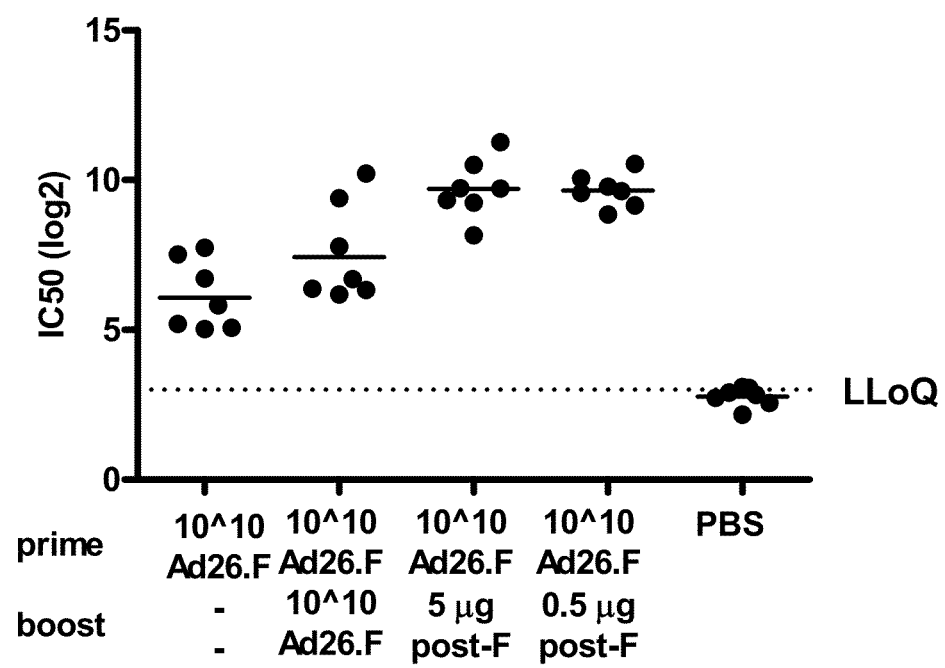
FIG. 25 shows the induction of virus neutralizing titers following immunization with rAd26 harboring the RSV F gene (Ad26.RSV.F) followed by boosting with Ad26.RSV.F or with adjuvanted RSV F protein (post-F).
Figure 26:
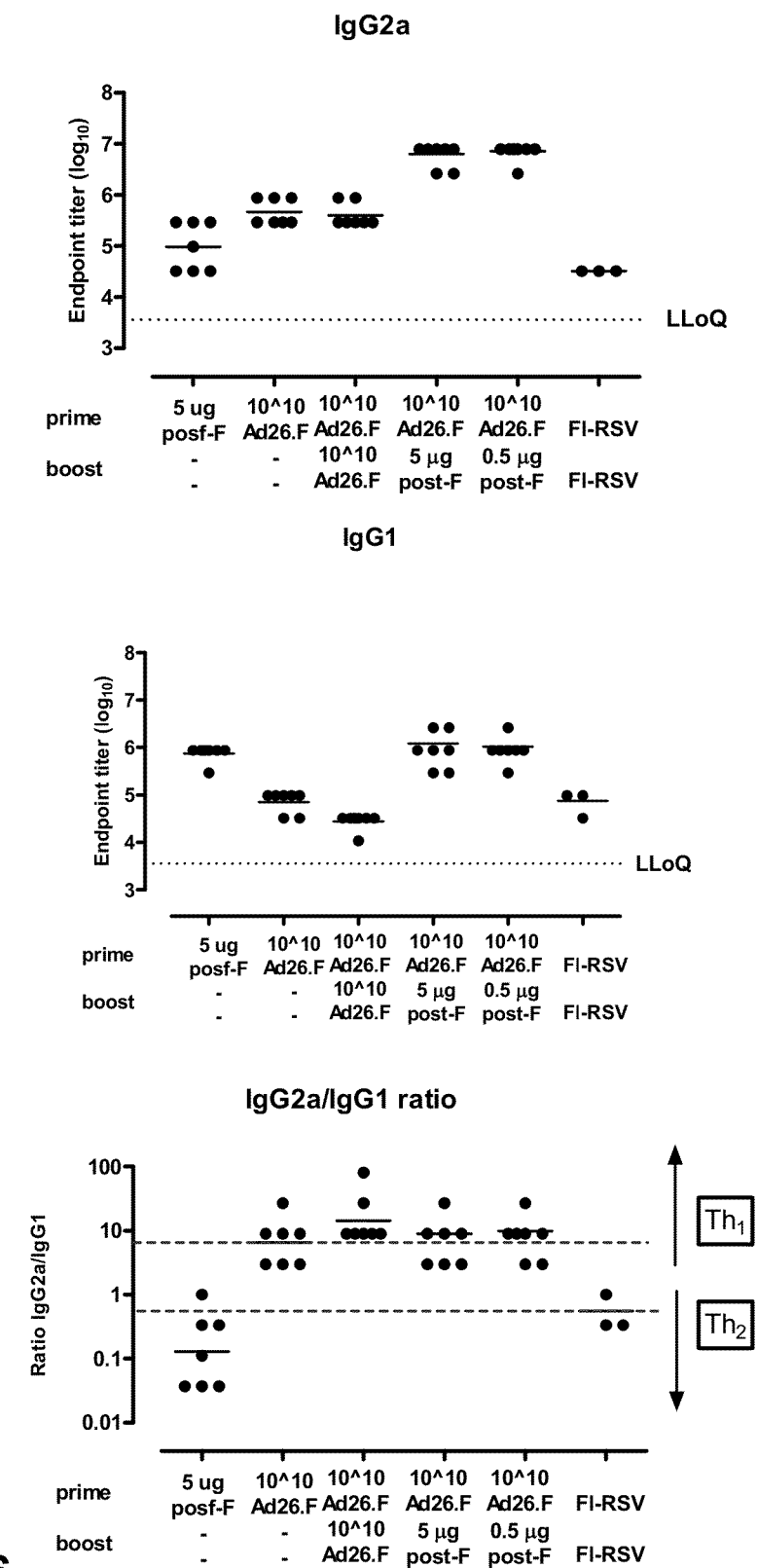
FIG. 26 shows the induction of IgG2a and IgG1 antibodies, and the ratio hereof, following immunization with Ad26.RSV.F followed by boosting with Ad26.RSV.F or by boosting with adjuvanted RSV F protein (post-F).
Figure 27:
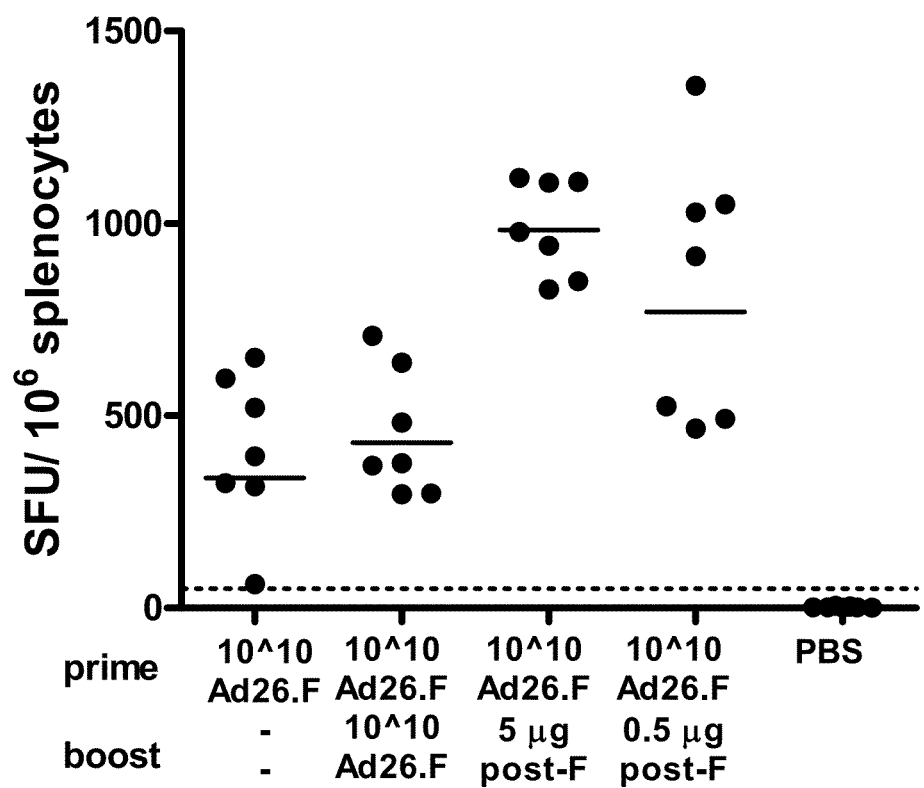
FIG. 27 shows the production of IFN-g by splenocytes following immunization with Ad26.RSV.F followed by boosting with Ad26.RSV.F or with adjuvanted RSV F protein (post-F).

Ad26.RSV.F Prime Boosted with Recombinant F Protein Results in a Th1 Skewed Response in a Mouse Model In this example, it was investigated whether the immune response upon Ad26.RSV.F prime can be enhanced by boosting with adjuvanted recombinant RSV F protein. To this aim mice were divided in experimental groups of 7 mice each. Animals were immunized at day 0 by intramuscular injections of $10^{10}$ viral particles (vp) adenoviral vectors carrying the full-length RSV F (A2) gene (Ad26.RSV.F) or PBS. At day 28 animals were boosted i.m. with either the same vector in the same dose, or with adjuvanted RSV F protein (full length; postfusion conformation: post-F) (in 2 doses: 5 µg and 0.5 µg). FIG. 25 clearly shows that serum derived from mice immunized with Ad26.RSV-F and boosted with adjuvanted RSV F shows high VNA titers at 12 weeks post immunization against RSV-A Long (subgroup A). FIG. 26 shows the IgG2a/IgG1 ratio in the sera of mice immunized with Ad26.RSV-$F_{A2}$ and boosted with adjuvanted RSV F protein. A high ratio is indicative of a Th1 balanced responses, whereas a low ratio indicates a Th2 skewed response. Clearly, Ad26.RSV.F immunized animals, boosted with either Ad26.RSV.F or RSV F protein results in a high IgG2a/IgG1 ratio, whereas control mice immunized with FI-RSV or RSV F protein (without the context of adenoviral vectors) induce a low ratio. Because a Th1 skewed response is strongly desired in an RSV vaccine to avoid enhanced disease upon challenge, the Th2 skewing response of a protein immunization can be directed towards a Th1 response when an Ad26.RSV.F prime is applied. FIG. 27 shows the cellular responses in spleens derived from mice immunized with Ad26.RSV-$F_{A2}$ and boosted with adjuvanted RSV F protein. It can clearly be observed that boosting with adjuvanted RSV F protein will strongly increase the cellular response as well. Based upon the earlier experiments described in the examples above, it is expected that substituting Ad26 with Ad35 will result in similar results.

TABLE 1 sequences

SEQ ID NO: 1: RSV fusion protein (Genbank ACO83301.1) peptide:
MELLILKANAITTILTAVTFCFASGQNITEEFYQSTCSAVSKGYLSALRTGWYTSVITIELS

NIKKNKCNGTDAKIKLIKQELDKYKNAVTELQLLMQSTPATNNRARRELPRFMNYTLN

NAKKTNVTLSKKRKRRFLGFLLGVGSAIASGVAVSKVLHLEGEVNKIKSALLSTNKAVV

SLSNGVSVLTSKVLDLKNYIDKQLLPIVNKQSCSISNIETVIEFQQKNNRLLEITREFSVNA

GVTTPVSTYMLTNSELLSLINDMPITNDQKKLMSNNVQIVRQQSYSIMSIIKEEVLAYVV

QLPLYGVIDTPCWKLHTSPLCTTNTKEGSNICLTRTDRGWYCDNAGSVSFFPQAETCKV

QSNRVFCDTMNSLTLPSEVNLCNVDIFNPKYDCKIMTSKTDVSSSVITSLGAIVSCYGKT

KCTASNKNRGIIKTFSNGCDYVSNKGVDTVSVGNTLYYVNKQEGKSLYVKGEPIINFYD

PLVFPSDEFDASISQVNEKINQSLAFIRKSDELLHNVNAVKSTTNIMITTIIIVIIVILLSLIAV

GLLLYCKARSTPVTLSKDQLSGINNIAFSN

SEQ ID NO: 2: codon optimized RSV.F(A2)nat gene that codes for
the RSV fusion protein:
ATGGAACTGCTGATCCTGAAGGCCAACGCCATCACCACCATCCTGACCGCCGTGACC

TTCTGCTTCGCCAGCGGCCAGAACATCACCGAGGAATTCTACCAGAGCACCTGTAGC

GCCGTGTCCAAGGGCTACCTGAGCGCCCTGCGGACCGGCTGGTACACCAGCGTGAT

CACCATCGAGCTGAGCAACATCAAAAAGAACAAGTGCAACGGCACCGACGCCAAA

ATCAAGCTGATCAAGCAGGAACTGGACAAGTACAAGAACGCCGTGACCGAGCTGCA

GCTGCTGATGCAGAGCACCCCCGCCACCAACAACCGGGCCAGACGGGAGCTGCCCC

GGTTCATGAACTACACCCTGAACAACGCCAAAAAGACCAACGTGACCCTGAGCAAG

AAGCGGAAGCGGCGGTTCCTGGGCTTCCTGCTGGGCGTGGGCAGCGCCATTGCTAG

CGGAGTGGCTGTGTCTAAGGTGCTGCACCTGGAAGGCGAAGTGAACAAGATCAAGT

CCGCCCTGCTGAGCACCAACAAGGCCGTGGTGTCCCTGAGCAACGGCGTGTCCGTG

CTGACCAGCAAGGTGCTGGATCTGAAGAACTACATCGACAAGCAGCTGCTGCCCAT

TABLE 1-continued sequences

CGTGAACAAGCAGAGCTGCAGCATCAGCAACATCGAGACAGTGATCGAGTTCCAGC

AGAAGAACAACCGGCTGCTGGAAATCACCCGCGAGTTCAGCGTGAACGCCGGCGTG

ACCACCCCCGTGTCCACCTACATGCTGACCAACAGCGAGCTGCTGAGCCTGATCAAC

GACATGCCCATCACCAACGACCAGAAAAAGCTGATGAGCAACAACGTGCAGATCGT

GCGGCAGCAGAGCTACTCCATCATGTCCATCATCAAAGAAGAGGTGCTGGCCTACG

TGGTGCAGCTGCCCCTGTACGGCGTGATCGACACCCCCTGCTGGAAGCTGCACACCA

GCCCCCTGTGCACCACCAACACCAAAGAGGGCAGCAACATCTGCCTGACCCGGACC

GACCGGGGCTGGTACTGCGATAATGCCGGCAGCGTGTCATTCTTTCCACAAGCCGAG

ACATGCAAGGTGCAGAGCAACCGGGTGTTCTGCGACACCATGAACAGCCTGACCCT

GCCCAGCGAGGTGAACCTGTGCAACGTGGACATCTTCAACCCTAAGTACGACTGCA

AGATCATGACCTCCAAGACCGACGTGTCCAGCTCCGTGATCACCTCCCTGGGCGCCA

TCGTGTCCTGCTACGGCAAGACCAAGTGCACCGCCAGCAACAAGAACCGGGGCATC

ATCAAGACCTTCAGCAACGGCTGCGACTACGTGTCCAACAAGGGCGTGGACACCGT

GTCCGTGGGCAACACCCTGTACTACGTGAACAAACAGGAAGGCAAGAGCCTGTACG

TGAAGGGCGAGCCCATCATCAACTTCTACGACCCCCTGGTGTTCCCCAGCGACGAGT

TCGACGCCAGCATCAGCCAGGTCAACGAGAAGATCAACCAGAGCCTGGCCTTCATC

AGAAAGAGCGACGAGCTGCTGCACAATGTGAATGCCGTGAAGTCCACCACCAATAT

CATGATCACCACAATCATCATCGTGATCATCGTCATCCTGCTGTCCCTGATCGCCGT

GGGCCTGCTGCTGTACTGCAAGGCCCGGTCCACCCCTGTGACCCTGTCCAAGGACCA

GCTGAGCGGCATCAACAATATCGCCTTCTCCAAC

---

What is claimed is:

1. A vaccine against respiratory syncytial virus (RSV), the vaccine comprising:
a recombinant human adenovirus of serotype 35 that comprises a nucleic acid molecule encoding an RSV F protein, wherein the nucleic acid molecule encoding RSV F protein comprises SEQ ID NO: 2.

2. A vaccine against respiratory syncytial virus (RSV), the vaccine comprising:
a recombinant human adenovirus of serotype 35 that comprises a nucleic acid molecule encoding a respiratory syncytial virus (RSV) F protein, wherein the nucleic acid molecule encoding RSV F protein comprises SEQ ID NO: 2, and wherein the recombinant human adenovirus has:
a deletion in the E1 region of the adenoviral genome, a deletion in the E3 region of the adenoviral genome, or a deletion in each of the E1 and the E3 regions of the adenoviral genome.

3. A method for vaccinating a subject against respiratory syncytial virus (RSV), the method comprising:
administering to the subject the vaccine of claim 2.

* * * * *

SEQUENCE LISTING

<160> NUMBER OF SEQ ID NOS: 2

<210> SEQ ID NO 1
<211> LENGTH: 574
<212> TYPE: PRT
<213> ORGANISM: respiratory syncytial virus
<220> FEATURE:
<221> NAME/KEY: RSV F protein (A2 strain)
<222> LOCATION: (1)..(574)

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro

```
            100                 105                 110
Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
            515                 520                 525
```

-continued

```
Thr Ile Ile Ile Val Ile Val Ile Leu Leu Ser Leu Ile Ala Val
            530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
                565                 570

<210> SEQ ID NO 2
<211> LENGTH: 1722
<212> TYPE: DNA
<213> ORGANISM: respiratory syncytial virus
<220> FEATURE:
<221> NAME/KEY: codon optimized sequence encoding RSV F protein (A2
      strain)
<222> LOCATION: (1)..(1722)

<400> SEQUENCE: 2
atggaactgc tgatcctgaa ggccaacgcc atcaccacca tcctgaccgc cgtgaccttc     60
tgcttcgcca gcggccagaa catcaccgag gaattctacc agagcacctg tagcgccgtg    120
tccaagggct acctgagcgc cctgcggacc ggctggtaca ccagcgtgat caccatcgag    180
ctgagcaaca tcaaaaagaa caagtgcaac ggcaccgacg ccaaaatcaa gctgatcaag    240
caggaactgg acaagtacaa gaacgccgtg accgagctgc agctgctgat gcagagcacc    300
cccgccacca caaccgggc cagacgggag ctgccccggt tcatgaacta caccctgaac    360
aacgccaaaa agaccaacgt gaccctgagc aagaagcgga agcggcggtt cctgggcttc    420
ctgctgggcg tgggcagcgc cattgctagc ggagtggctg tgtctaaggt gctgcacctg    480
gaaggcgaag tgaacaagat caagtccgcc ctgctgagca ccaacaaggc cgtggtgtcc    540
ctgagcaacg gcgtgtccgt gctgaccagc aaggtgctgg atctgaagaa ctacatcgac    600
aagcagctgc tgcccatcgt gaacaagcag agctgcagca tcagcaacat cgagacagtg    660
atcgagttcc agcagaagaa caaccggctg ctggaaatca cccgcgagtt cagcgtgaac    720
gccggcgtga ccaccccccgt gtccacctac atgctgacca cagcgagct gctgagcctg    780 atcaacgaca tgcccatcac caacgaccag aaaaagctga tgagcaacaa cgtgcagatc    840
gtgcggcagc agagctactc catcatgtcc atcatcaaag aagaggtgct ggcctacgtg    900
gtgcagctgc ccctgtacgg cgtgatcgac accccctgct ggaagctgca caccagcccc    960
ctgtgcacca ccaacaccaa agagggcagc aacatctgcc tgacccggac cgaccggggc   1020
tggtactgcg ataatgccgg cagcgtgtca ttctttccac aagccgagac atgcaaggtg   1080
cagagcaacc gggtgttctg cgacaccatg aacagcctga cctgcccag cgaggtgaac   1140 ctgtgcaacg tggacatctt caaccctaag tacgactgca agatcatgac ctccaagacc   1200
gacgtgtcca gctccgtgat cacctccctg ggcgccatcg tgtcctgcta cggcaagacc   1260
aagtgcaccg ccagcaacaa gaaccggggc atcatcaaga ccttcagcaa cggctgcgac   1320
tacgtgtcca caagggcgt ggacaccgtg tccgtgggca cacccctgta ctacgtgaac   1380
aaacaggaag gcaagagcct gtacgtgaag ggcgagccca tcatcaactt ctacgacccc   1440
ctggtgttcc ccagcgacga gttcgacgcc agcatcagcc aggtcaacga gaagatcaac   1500
cagagcctgg ccttcatcag aaagagcgac gagctgctgc acaatgtgaa tgccgtgaag   1560
tccaccacca atatcatgat caccacaatc atcatcgtga tcatcgtcat cctgctgtcc   1620
```

```
ctgatcgccg tgggcctgct gctgtactgc aaggcccggt ccacccctgt gaccctgtcc    1680
aaggaccagc tgagcggcat caacaatatc gccttctcca ac                      1722
```